United States Patent
Campbell, Jr. et al.

(10) Patent No.: US 6,716,786 B1
(45) Date of Patent: *Apr. 6, 2004

(54) SUPPORTED CATALYST COMPRISING EXPANDED ANIONS

(75) Inventors: Richard E. Campbell, Jr., Midland, MI (US); Grant B. Jacobsen, Houston, TX (US); David D. Devore, Midland, MI (US); Robert E. LaPointe, Midland, MI (US); David R. Neithamer, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 441 days.

This patent is subject to a terminal disclaimer.

(21) Appl. No.: 09/631,654

(22) Filed: Aug. 3, 2000

Related U.S. Application Data

(63) Continuation of application No. 09/251,664, filed on Feb. 17, 1999, now abandoned.
(60) Provisional application No. 60/156,242, filed on Sep. 27, 1999, and provisional application No. 60/075,329, filed on Feb. 10, 1998.

(51) Int. Cl.$^7$ ............... B01J 31/00; B01J 37/00; C08F 4/02; C08F 4/60; C08F 4/44
(52) U.S. Cl. ............... 502/103; 502/117; 502/155; 502/167; 526/134; 526/160; 526/165; 526/943
(58) Field of Search ............... 502/103, 117, 502/155, 167; 526/134, 160, 165, 943

(56) References Cited

U.S. PATENT DOCUMENTS

| | | | |
|---|---|---|---|
| 4,543,399 A | 9/1985 | Jenkins, III et al. | |
| 5,132,380 A | 7/1992 | Stevens et al. | |
| 5,153,157 A | 10/1992 | Hlatky et al. | |
| 5,189,192 A | 2/1993 | LaPointe et al. | |
| 5,198,401 A | 3/1993 | Turner et al. | |
| 5,321,106 A | 6/1994 | LaPointe | |
| 5,350,723 A | 9/1994 | Neithamer et al. | |
| 5,352,749 A | 10/1994 | DeChellis et al. | |
| 5,407,884 A | 4/1995 | Turner et al. | |
| 5,447,895 A | 9/1995 | Marks et al. | |
| 5,470,927 A | 11/1995 | Turner et al. | |
| 5,625,087 A | 4/1997 | Devore et al. | |
| 6,395,671 B2 * | 5/2002 | LaPointe | 502/150 |
| 6,462,156 B2 * | 10/2002 | LaPointe | 526/165 |

FOREIGN PATENT DOCUMENTS

| | | |
|---|---|---|
| EP | 0089 691 B1 | 11/1989 |
| EP | 520732 | 12/1995 |
| EP | 824113 | 2/1998 |
| EP | 924223 | 6/1999 |
| WO | WO 94/25495 A1 | 11/1994 |
| WO | WO 94/28032 A1 | 12/1994 |
| WO | WO 99/42467 | 8/1999 |

OTHER PUBLICATIONS

*J. Am. Chem. Soc.*, Marks et al, vol. 118, pp. 12451–12452, 1996.
International Preliminary Examination Report, Oct. 31, 2001.

* cited by examiner

*Primary Examiner*—Mark L. Bell
*Assistant Examiner*—J. Pasterczyk
(74) *Attorney, Agent, or Firm*—Jenkens & Gilchrist

(57) ABSTRACT

A composition useful as an addition polymerization catalyst comprising:

A) an inert support;
B) a Group 3–10 or Lanthanide metal complex; and
C) an activator compound capable of causing the metal complex B) to form an active polymerization catalyst, said compound corresponding to the formula:

$$(A^{*+a})_b (Z^* J^*_j)^{-c}{}_d, \qquad (I)$$

wherein:
$A^*$ is a cation of charge $+a$,
$Z^*$ is an anion group of from 1 to 50, preferably 1 to 30 atoms, not counting hydrogen atoms, further containing two or more Lewis base sites;
$J^*$ independently each occurrence is a Lewis acid coordinated to at least one Lewis base-site of $Z^*$, and optionally two or more such $J^*$ groups may be joined together in a moiety having multiple Lewis acidic functionality,
$j$ is a number from 2 to 12 and
$a$, $b$, $c$, and $d$ are integers from 1 to 3, with the proviso that $a \times b$ is equal to $c \times d$.

14 Claims, No Drawings

SUPPORTED CATALYST COMPRISING EXPANDED ANIONS

CROSS REFERENCE STATEMENT

This application is a cont. application Ser. No. 09/251,664, filed on Feb. 17, 1999, now abandoned, which claims the benefit of U.S. Provisional Application No. 60/075,329, filed Feb. 20, 1998. This application also claims the benefit of U.S. Provisional Application 60/156,242, filed Sep. 27, 1999.

BACKGROUND INFORMATION

The present invention relates to catalyst compositions that are particularly adapted for use in the polymerization of olefins and other addition polymerizable monomers under slurry, high pressure or gas phase polymerization conditions. More particularly, the present invention relates to catalyst compositions comprising a support material, a metal complex catalyst, and an activator compound comprising an anion containing at least two Lewis basic sites that are coordinated to Lewis acids.

It is previously known in the art to activate Ziegler-Natta Polymerization catalysts, particularly such catalysts comprising Group 3–10 metal complexes containing delocalized π-bonded ligand groups, by the use of Bronsted acid salts capable of transferring a proton to form a cationic derivative or other catalytically active derivative of such Group 3–10 metal complex Preferred Bronsted acid salts are such compounds containing a cation/anion pair that is capable of rendering the Group 3–10 metal complex catalytically active. Suitable activators comprise fluorinated arylborate anions, such as tetrakis(pentafluorophenyl)borate. Additional suitable anions include sterically shielded diboron anions of the formula:

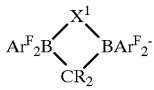

wherein:
R is a hydrogen, alkyl, fluoroalkyl, aryl, or fluoroaryl, $Ar^F$ is fluoroaryl, and $X^1$ is either hydrogen or halide, disclosed in U.S. Pat. No. 5,447,895. Additional examples include carborane compounds such as are disclosed and claimed in U.S. Pat. No. 5,407,884.

Examples of preferred charge separated (cation/anion pair) activators are ammonium, sulfonium, or phosphonium salts capable of transferring a hydrogen ion, disclosed in U.S. Pat. Nos. 5,198,401, 5,132,380, 5,470,927 and 5,153,157, as well as oxidizing salts such as ferrocenium, silver or lead salts, disclosed in U.S. Pat. Nos. 5,189,192 and 5,321,106 and strongly Lewis acidic salts such as carbonium or silylium salts, disclosed in U.S. Pat. Nos. 5,350,723 and 5,625,087.

Further suitable activators for the above metal complexes include strong Lewis acids including tris(perfluorophenyl) borane and tris(perfluorobiphenyl)borane. The former composition has been previously disclosed for the above stated end use in EP-A-520,732, whereas the latter composition is similarly disclosed by Marks, et al., in *J. Am. Chem. Soc.*, 118, 12451–12452 (1996). Catalyst activator compounds comprising an anion containing at least two Lewis basic sites which are coordinated to Lewis acids and their use in the polymerization of unsaturated compounds by means of any suitable process including a slurry or gas phase polymerization are disclosed in U. S. provisional application No. 60/75329, and in U.S. Ser. No. 09/251664, filed Feb. 17, 1999.

SUMMARY OF THE INVENTION

According to the present invention there are now provided supported catalyst compositions for use in an addition polymerization comprising:

A) an inert support;
B) a Group 3–10 or Lanthanide metal complex; and
C) an activator compound capable of causing the metal complex B) to form an active polymerization catalyst, said compound corresponding to the formula:

wherein:
$A^*$ is a cation of charge $+a$,
$Z^*$ is an anion group of from 1 to 50, preferably 1 to 30 atoms, not counting hydrogen atoms, further containing two or more Lewis base sites;
$J^*$ independently each occurrence is a Lewis acid coordinated to at least one Lewis base site of $Z^*$, and optionally two or more such $J^*$ groups may be joined together in a moiety having multiple Lewis acidic functionality,
j is a number from 2 to 12 and
a, b, c, and d are integers from 1 to 3, with the proviso that a×b is equal to c×d.

Additionally according to the present invention there is provided a process for polymerization of one or more addition polymerizable monomers, especially ethylenically unsaturated monomers, most preferably, $C_{2-20,000}$ α-olefins, comprising contacting the same, optionally in the presence of an inert aliphatic, alicyclic or aromatic hydrocarbon, with the above catalyst composition under continuous or semi-continuous solution, high pressure, slurry, bulk or gas phase polymerization conditions.

The foregoing supported catalyst compositions are uniquely adapted for use under slurry polymerization conditions and uniquely produce polymers of high bulk density with low reactor fouling. In addition, the foregoing compositions and processes are highly desirable for use in the gas phase polymerization of olefins, particularly ethylene or propylene and combinations of ethylene with a $C_{3-8}$ α-olefin.

DETAILED DESCRIPTION OF THE INVENTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups. When mentioned herein, the teachings of any patent, patent application or publication are hereby incorporated by reference.

The activator compound of formula (I), component C), is further characterized in the following manner. $A^{*+a}$ is desirably chosen to provide overall neutrality to the compound and to not interfere with subsequent catalytic activity. Moreover, the cation may participate in the formation of the active catalyst species, desirably through a proton transfer, oxidation, or ligand abstraction mechanism, or a combination thereof.

Examples of suitable cations include ammonium, sulfonium, phosphonium, oxonium, carbonium, and silylium cations, preferably those containing up to 80 atoms not counting hydrogen, as well as ferrocenium, $Ag^+$, $Pb^{+2}$, or similar oxidizing cations. In a preferred embodiment, a, b, c and d are all equal to one.

$Z^*$ can be any anionic moiety containing two or more Lewis basic sites. Preferably, the Lewis base sites are on different atoms of a polyatomic anionic moiety. Desirably, such Lewis basic sites are relatively sterically accessible to the Lewis acid, $J^*$. Preferably the Lewis basic sites are on nitrogen or carbon atoms. Examples of suitable $Z^*$ anions include cyanide, azide, amide and substituted amide, amidinide and substituted amidinide, dicyanamide, imidazolide, substituted imidazolide, imidazolinide, substituted imidazolinide, benzimidazolide, substituted benzimidazolide, tricyanomethide, tetracyanoborate, puride, squarate, 1,2,3-triazolide, substituted 1,2,3-triazolide, 1,2,4-triazolide, substituted 1,2,4-triazolide, 4,5-benzi-1,2,3-triazolide, substituted 4,5-benzi-1,2,3-triazolide, pyrimidinide, substituted pyrimidinide, tetraimidazoylborate and substituted tetraimidazoylborate anions, wherein each substituent, if present, is a halo, hydrocarbyl, halohydrocarbyl, silyl, (including mono-, di- and tri(hydrocarbyl)silyl), silylhydrocarbyl, or halocarbyl group of up to 20 atoms not counting hydrogen, or two such substituents together form a saturated or unsaturated ring system.

Specific examples of $Z^*$ groups include: imidazolide, 2-nonadecylimidazolide, 2-undecylimidazolide, 2-tridecylimidazolide, 2-pentadecylimidazolide, 2-heptadecylimidazolide, 2-nonadecylimidazolide, 4,5-difluoroimidazolide, 4,5-dichloroimidazolide, 4,5-dibromoimidazolide, 4,5-bis(heptadecyl)imidazolide, 4,5-bis(undecyl)imidazolide, imidazolinide, 2-nonadecylimidazolinide, 2-undecylimidazolinide, 2-tridecylimidazolinide, 2-pentadecylimidazolinide, 2-heptadecylimidazolinide, 2-nonadecylimidazolinide, 4,5-difluoroimidazolinide, 4,5-dichloroimidazolinide, 4,5-dibromoimidazolinide, 4,5-bis(heptadecyl)imidazolinide, 4,5-bis(undecyl)imidazolinide, didecylamide, piperidinide, 4,4-dimethylimidazolinide, tetra-5-pyrimidinylborate, pyrimidinide, 2-undecylbenzimidazolide, 5,6-dichlorobenzimidazolide, 4,5-dicyanoimidazolide, and 5,6-dimethylbenzimidazolide anions.

Preferred $Z^*$ groups for the formation of the supported catalysts of the present invention are imidazolide, 2-undecylimidazolide, 1,2,3-triazolide, substituted 1,2,3-triazolide, 1,2,4-triazolide, substituted 1,2,4-triazolide, 4,5-benzi-1,2,3-triazolide, and substituted 4,5-benzi-1,2,3-triazolide, where the substituents are halo, silyl or $C_{1-20}$ hydrocarbyl, especially $C_{1-20}$ alkyl or phenyl. A particularly preferred $Z^*$ group is the 1,2,4-triazolide group.

Coordinated to the Lewis base sites of the anion are from 2 to 12 Lewis acids, $J^*$, two or more of which may be joined together in a moiety having multiple Lewis acidic functionality. Preferably, from 2 to 4 $J^*$ groups having from 3 to 100 atoms not counting hydrogen are present.

More specific examples of the foregoing Lewis acid compounds, $J^*$, correspond to the formula:

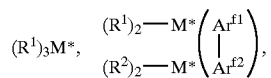

-continued

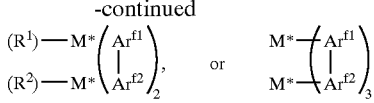

wherein:
  $M^*$ is aluminum, gallium or boron;
  $R^1$ and $R^2$ independently each occurrence are hydride, halide, or a hydrocarbyl, halocarbyl, halohydrocarbyl, dialkylamido, alkoxide, or aryloxide group of up to 20 carbons, with the proviso that in not more than one occurrence is $R^1$ or $R^2$ halide, and
  $Ar^{f1}$—$Ar^{f2}$ in combination, independently each occurrence, is a divalent fluoro-substituted aromatic group of from 6 to 20 carbons.

Highly preferred Lewis acids are aluminum or boron compounds corresponding to the formula: $M^*R^1_3$, wherein $R^1$ independently each occurrence is selected from hydrocarbyl, halocarbyl, and halohydrocarbyl radicals, said $R^1$ having up to 20 carbons. In a more highly preferred embodiment, $R^1$ is a fluorinated aryl group, especially, pentafluorophenyl, and $M^*$ is Al.

Examples of the foregoing Lewis acid groups containing multiple Lewis acid sites are:

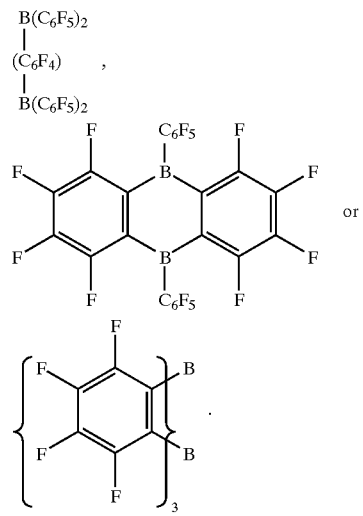

Suitable activator compounds according to the present invention include the ammonium, phosphonium, sulfonium, oxonium, carbonium, silylium, lead (II), silver or ferrocenium salts of: bis(tris(pentafluorophenyl)alumane)cyanide, bis(tris(pentafluorophenyl)alumane)azide, bis(tris (pentafluorophenyl)-alumane)dicyanamide, bis(tris (pentafluorophenyl)alumane)imidazolide, bis(tris(pentafluorophenyl)alumane)-2-undecylimidazolide, bis(tris (pentafluorophenyl)alumane)-4,5-dichloroimidazolide, bis (tris(penta-fluorophenyl)alumane)-2-undecyl-4,5-dichloroimidazolide, bis(tris(pentafluorophenyl)alumane)4,5-diphenylimidazolide, bis(tris(penta-fluorophenylalumane)-2-undecyl-4,5-diphenylimidazolide, bis(tris(pentafluorophenyl)alumane)imidazolinide, bis(tris (pentafluorophenyl)alumane)-2-undecylimidazolinide, bis (tris-(pentafluorophenyl)alumane)-5,6-dimethylbenzimidazolide, bis(tris(pentafluorophenyl) alumane)-4,5-bis(heptadecyl)imidazolide, tris(tris (pentafluorophenyl)alumanetricyanomethide, tris(tris (pentafluorophenyi)alumane)puride, tetrakis(tris (pentafluoro-phenyl)alumane)tetraimidazoylborate, bis(tris (heptafluoro-2-naphthyl)alumane)cyanide, bis(tris (heptafluoro-2-naphthyl)alumane)azide, bis(tris(heptafluoro-2-naphthyl)alumane)dicyanamide, bis(tris (heptafluoro-2-naphthyl)alumane)imidazolide, bis(tris (heptafluoro-2-naphthyl)alumane)-2-undecylimidazolide, bis(tris(pentafluorophenylalumane)benzimidazolide, bis(tris (penta-fiuorophenyl)alumane)-2-undecylbenzimidazolide, bis(tris-(heptafluoro-2-naphthyl)alumane)-5,6-dimethylbenzimidazolide, bis(tris(heptafluoro-2-naphthyl) alumane)-4,5-bis(heptadecyl)imidazolide, tris (trisheptafluoro-2-naphthyl)-alumanetricyanomethide, tris (tris(heptafluoro-2-naphthyl)alumane)puride, tetrakis(tris (heptafluoro-2-naphthyl)alumane)tetraimidazoylborate, bis (tris(pentafluorophenyl)alumane)-1,2,3-triazolide, bis(tris (pentafluorophenyl)alumane)-1,2,4-triazolide, bis(tris (pentafluorophenyl)alumane)-4,5-diphenyl-1,2,3-triazolide, bis(tris(pentafluorophenyi)alumane)-1,2,3-benzatriazolide, bis(tris(pentafluorophenyl)alumane)-5-methyl-1,2,4-triazolide, bis(tris(pentafluorophenyl)alumane)-5-undecyl-1,2,4-triazolide, bis(tris(pentafluorophenyl)borane)cyanide, bis(tris(pentafluorophenyl)borane)azide, bis(tris (pentafluorophenyl)borane)dicyanamide, bis(tris (pentafluorophenyl)borane)imidazolide, bis(tris(pentafluorophenyl)borane)-2-undecylimidazolide, bis(tris (pentafluorophenyl)borane)-4,5-dichloroimidazolide, bis (tris(penta-fluorophenyl)borane)-2-undecyl-4,5-dichloroimidazolide, bis(tris(pentafluorophenyl)borane)4,5-diphenylimidazolide, bis(tris(pentafluorophenyl)borane)-2-undecyl-4,5-diphenylimidazolide, bis(tris (pentafluorophenyl)borane)imidazolinide, bis(tris (pentafluorophenyl)borane)-2-undecylimidazolinide, bis (tris(pentafluorophenyl)borane)-5,6-dimethylbenzimidazolide, bis(tris(pentafluorophenyl) borane)-4,5-bis(heptadecyl)imidazolide, tris(tris (pentafluorophenyl)borane tricyanomethide, tris(tris (pentafluorophenyl)borane)puride, tetrakis(tris (pentafluorophenyl)borane)tetraimidazoylborate, bis(tris (heptafluoro-2-naphthyl)borane)cyanide, bis(tris (heptafluoro-2-naphthyl)borane)azide, bis(tris(hepta-fluoro-2-naphthyl)borane)dicyanamide, bis(tris(heptafluoro-2-naphthyl)borane)imidazolide, bis(tris(heptafluoro-2-naphthyl)borane)-2-undecylimidazolide, bis(tris (pentafluorophenyl)borane)benzimidazolide, bis(tris(pentafluorophenyl)borane)-2-undecylbenzimidazolide, bis(tris-(heptafluoro-2-naphthyl)borane)-5,6-dimethylbenzimidazolide, bis(tris(heptafluoro-2-naphthyl) borane)-4,5-bis(heptadecyl)imidazolide, tris (trisheptafluoro-2-naphthyl)borane tricyanomethide, tris(tris (heptafluoro-2-naphthyl)borane)puride, tetrakis(tris (heptafluoro-2-naphthyl)borane)tetraimidazoylborate, bis (tris(pentafluorophenyl)borane)-1,2,3-benzatriazolide, bis (tris(pentafluorophenyl)borane)-1,2,4-triazolide, bis(tris (pentafluorophenyl)borane)-4,5-diphenyl-1,2,3-triazolide, bis(tris(pentafluorophenyl)borane-5-methyl-1,2,4-triazolide, and bis (tris(pentafluorophenyl)borane)-5-undecyl-1,2,4-triazolide.

Preferred activator compounds are the foregoing ammonium salts, especially those which comprise trihydrocarbyl-substituted ammonium cations, especially trimethylammonium-, triethylammonium-, tripropylammonium-, tri(n-butyl)ammonium-, methyldi (octadecyl)ammonium-, methyldi(tetradecyl)ammonium-, methyl(tetradecyl)(octadecyl)ammonium-, N,N-dimethylanilinium-, N,N-di(ethyl)anilinium-, N,N-di (methyl)2,4,6-trimethylanilinium-, N,N-di(octadecyl) anilinium-, N,N-di(tetradecyl)anilinium-, N,N-di (octadecyl)-2,4,6-tri(methyl)anilinium-, and methyldi (cyclohexyl)ammonium-cations or mixtures thereof.

Most preferred ammonium cation containing salts are those containing trihydrocarbyl-substituted ammonium cations containing one or two $C_{10}$-$C_{40}$ alkyl groups, especially methyldi(octadecyl)ammonium-, di(octadecyl)anilinium-, di(octadecyl)-2,4,6-tri(methyl)anilinium-, and methyldi (tetradecyl)ammonium-cations. It is further understood that the cation may comprise a mixture of hydrocarbyl groups of differing lengths. For example, the protonated ammonium cation derived from the commercially available long chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT.

The foregoing activator compounds (illustrated by those having imidazolide, substituted imidazolide, imidazolinide, substituted imidazolinide, benzimidazolide, substituted benzimidazolide, triazolide, substituted triazolide, benzatriazolide, or substituted benzatriazolide anions) may be depicted schematically as follows:

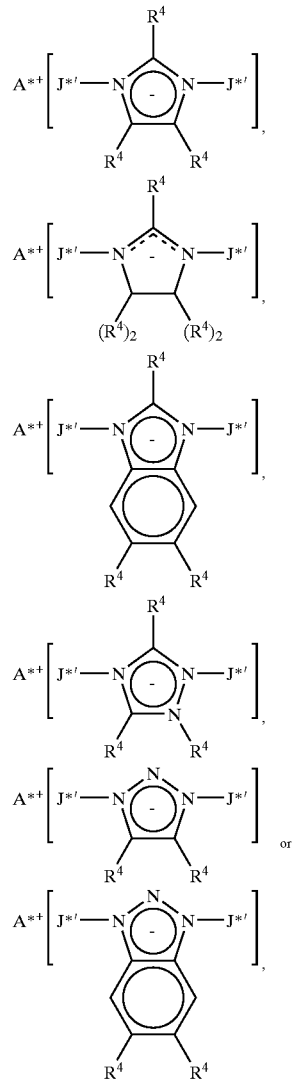

wherein:
A$^{*+}$ is a monovalent cation as previously defined, and preferably is a trihydrocarbyl ammonium cation, containing one or two $C_{10-40}$ alkyl groups, especially the methylbis(tetradecyl)ammonium- or methylbis(octadecyl)ammonium-cation, or a mixture thereof, R$^4$, independently each occurrence, is hydrogen or a halo, hydrocarbyl, halocarbyl, halohydrocarbyl, silylhydrocarbyl, or silyl group, (including mono-, di- and tri(hydrocarbyl)silyl) groups of up to 30 atoms not counting hydrogen, preferably a C$_{1-20}$ alkyl group, and J*, is tris(pentafluorophenyl)borane or tris(pentafluorophenyl)alumane).

Examples of the most highly preferred catalyst activators herein include the forgoing tri(C$_{1-20}$hydrocarbyl)ammonium-, especially, methylbis(tetradecyl)ammonium- or methylbis(octadecyl)ammonium-salts (or mixtures thereof) of:

bis(tris(pentafluorophenyl)borane)imidazolide,
bis(tris(pentafluorophenyl)borane)-2-undecylimidazolide,
bis(tris(pentafluorophenyl)borane)benzimidazolide,
bis(tris(pentafluorophenyl)borane)-2-undecylbenzimidazolide,
bis(tris(pentafluorophenyl)borane)imidazolinide,
bis(tris(pentafluorophenyl)borane)2-undecylimidazolinide,
bis(tris(pentafluorophenyl)borane)-1,2,3-triazolide,
bis(tris(pentafluorophenyl)borane)-1,2,4-triazolide,
bis(tris(pentafluorophenyl)borane)-3-(undecyl)-1,2,4-triazolide,
bis(tris(pentafluorophenyl)alumane)imidazolide,
bis(tris(pentafluorophenyl)alumane)-2-undecylimidazolide,
bis(tris(pentafluorophenyl)alumane)benzimidazolide,
bis(tris(pentafluorophenyl)alumane)-2-undecylbenzimidazolide,
bis(tris(pentafluorophenyl)alumane)imidazolinide,
bis(tris(pentafluorophenyl)alumane)2-undecylimidazolinide,
bis(tris(pentafluorophenyl)alumane)-1,2,3-triazolide,
bis(tris(pentafluorophenyl)alumane)-1,2,4-triazolide, and
bis(tris(pentafluorophenyl)alumane)-3-(undecyl)-1,2,4-triazolide .

The activator compounds may be prepared by a condensation reaction between the alkali metal salt of the anion, Z*, and a Lewis acid, J*, preferably under phase transfer conditions, using for example a crown ether to solubilize the alkali metal salt, followed by a metathesis reaction with the corresponding halide salt of the cation, A*$^{+a}$. Certain of the activator compounds are also amenable to preparation via a one step, single reactor process. For example, the ammonium or phosphonium imidiazolide, or substituted imidiazolide salts can be prepared by contacting the Lewis acid, J*, or its Lewis base adduct, such as an etherate, with the neutral compound corresponding to the anion, Z*. Both reactants are desirably relatively lipophilic, such that the reaction can be performed in non-polar solvents. Addition of the free base corresponding to the cation, A*$^{+a}$, results in formation of the charge separated species, which may be recovered from the reaction mixture by devolatilization or used without recovery or further purification.

Suitable metal complexes for use as component B) in the present invention include any compound or complex of a metal of Groups 3–10 or the Lanthanide series of the Periodic Table of the Elements capable of being activated to polymerize ethylenically unsaturated compounds by the present activators. Examples include Group 10 diimine derivatives corresponding to the formula:

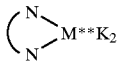

wherein

M** is Ni(II) or Pd(II);

K is halo, hydrocarbyl, or hydrocarbyloxy;

and the two nitrogen atoms are linked by a bridging system.

Such complexes have been previously disclosed in *J. Am. Chem. Soc.*, 118, 267–268 (1996), *J. Am. Chem. Soc.*, 117, 6414–6415 (1995), and *Organometallics*, 16, 1514–1516, (1997).

Additional catalysts include derivatives of Group 3, 4, or Lanthanide metals which are in the +2, +3, or +4 formal oxidation state. Preferred compounds include metal complexes containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, phosphole, and arene groups. By the term "π-bonded" is meant that the ligand group is bonded to the transition metal by a sharing of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are C$_{1-20}$ straight, branched and cyclic alkyl radicals, C$_{6-20}$ aromatic radicals, C$_{7-20}$ alkyl-substituted aromatic radicals, and C$_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, e. g. amide, phosphide, ether or thioether groups bonded to the transition metal or Lanthanide metal, and bonded to the hydrocarbyl group or to the hydrocarbyl- substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, phosphole, and boratabenzene groups, as well as hydrocarbyl- silyl- (including mono-, di-, or tri(hydrocarbyl) silyl) substituted derivatives thereof. Preferred anionic, delocalized π-bonded groups are cyclopentadienyl, pentamethylcyclopentadienyl, tetramethylcyclopentadienyl, tetramethyl(trimethylsilyl)-cyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands that are boron containing analogues to benzene. They are previously known in the art having been described by G. Herberich, et al., in *Organometallics*, 14,1, 471–480 (1995). Preferred boratabenzenes correspond to the formula:

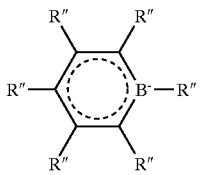

wherein R" is selected from the group consisting of hydrocarbyl, silyl, N,N-dihydrocarbylamino, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

Phospholes are anionic ligands that are phosphorus containing analogues to a cyclopentadienyl group. They are previously known in the art having been described by WO 98/50392, and elsewhere. Preferred phosphole ligands correspond to the formula:

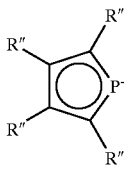

wherein R" is selected from the group consisting of hydrocarbyl, silyl, N,N-dihydrocarbylamino, or germyl, said R" having up to 20 non-hydrogen atoms, and optionally one or more R" groups may be bonded together forming a multicyclic fused ring system, or form a bridging group connected to the metal. In complexes involving divalent derivatives of such delocalized π-bonded groups one atom thereof is bonded by means of a covalent bond or a covalently bonded divalent group to another atom of the complex thereby forming a bridged system.

Phosphinimine/cyclopentadienyl complexes are disclosed in EP-A-890581 and correspond to the formula [(R)$_3$—P=N]$_{b'}$M*(Cp)(L$^1$)$_{3-b'}$, wherein:

R is a monovalent ligand, illustrated by hydrogen, halogen, or hydrocarbyl, or two R groups together form a divalent ligand, b' is 1 or 2;

M*** is a Group 4 metal,

Cp is cyclopentadienyl, or similar delocalized π-bonded group,

L$^1$ is a monovalent ligand group, illustrated by hydrogen, halogen or hydrocarbyl, and n is 1 or 2.

A suitable class of catalysts are transition metal complexes corresponding to the formula:

Lp$_l$MX$_m$X'$_n$X"$_p$, or a dimer thereof wherein:

Lp is an anionic, delocalized, π-bonded group that is bound to M, containing up to 50 non-hydrogen atoms, optionally two Lp groups may be joined together forming a bridged structure, and further optionally one Lp may be bound to X;

M is a metal of Group 4 of the Periodic Table of the Elements in the +2, +3 or +4 formal oxidation state;

X is an optional, divalent substituent of up to 50 non-hydrogen atoms that together with Lp forms a metallocycle with M;

X' is an optional neutral ligand having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or, optionally 2 X" groups may be covalently bound together to form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 0, 1 or 2;

m is 0 or 1;

n is a number from 0 to 3;

p is an integer from 0 to 3; and the sum, l+m+p, is equal to the formal oxidation state of M, except when 2 X" groups together form a neutral conjugated or non-conjugated diene that is π-bonded to M, in which case the sum l+m is equal to the formal oxidation state of M.

Preferred complexes include those containing either one or two Lp groups. The latter complexes include those containing a bridging group linking the two Lp groups. Preferred bridging groups are those corresponding to the formula (ER*$_2$)$_x$ wherein E is silicon, germanium, tin, or carbon, R* independently each occurrence is hydrogen or a group selected from silyl, hydrocarbyl, hydrocarbyloxy and combinations thereof, said R* having up to 30 carbon or silicon atoms, and x is 1 to 8. Preferably, R* independently each occurrence is methyl, ethyl, propyl, benzyl, tert-butyl, phenyl, methoxy, ethoxy or phenoxy.

Examples of the complexes containing two Lp groups are compounds corresponding to the formula:

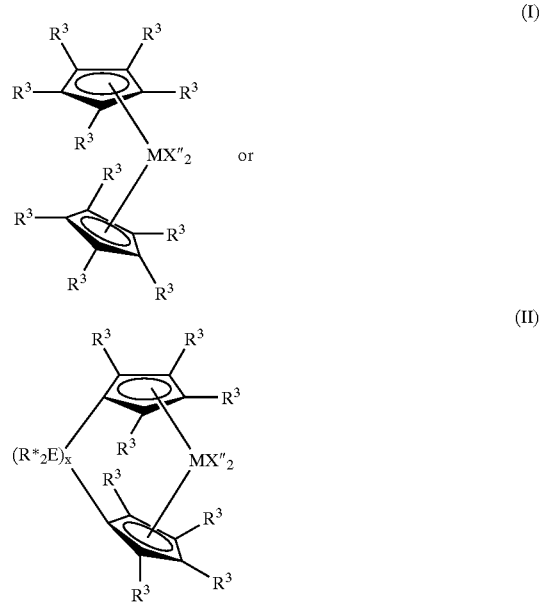

wherein:

M is titanium, zirconium or hafnium, preferably zirconium or hafnium, in the +2 or +4 formal oxidation state;

R³ in each occurrence independently is selected from the group consisting of hydrogen, hydrocarbyl, silyl, germyl, cyano, halo and combinations thereof, said R³ having up to 20 non-hydrogen atoms, or adjacent R³ groups together form a divalent derivative (that is, a hydrocarbadiyl, siladiyl or germadiyl group) thereby forming a fused ring system, and X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, and R*, E and x are as previously defined.

The foregoing metal complexes are especially suited for the preparation of polymers having stereoregular molecular structure. In such capacity it is preferred that the complex possesses $C_s$ symmetry or possesses a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include rac bis-indenyl complexes. Similar systems based on Ti(IV) or Zr(IV) were disclosed for preparation of isotactic olefin polymers in Wild et al., *J. Organomet. Chem.*, 232, 233–47, (1982).

Exemplary bridged ligands containing two π-bonded groups are: dimethylbis(cyclopentadienyl)silane, dimethylbis(tetramethylcyclopentadienylesilane, dimethylbis(2-ethylcyclopentadien-1-yl)silane, dimethylbis(2-t-butylcyclopentadien-1-yl)silane, 2,2-bis(tetramethylcyclopentadienyl)propane, dimethylbis(inden-1-yl)silane, dimethylbis(tetrahydroinden-1-yl)silane, dimethylbis(fluoren-1-yl)silane, dimethylbis(tetrahydrofluoren-1-yl)silane, dimethylbis(2-methyl-4-phenylinden-1-yl)-silane, dimethylbis(2-methylinden-1-yl) silane, dimethyl(cyclopentadienyl)(fluoren-1-yl)silane, dimethyl(cyclopentadienyl)(octahydrofluoren-1-yl)silane, dimethyl(cyclopentadienyl)(tetrahydrofluoren-1-yl)silane, (1,1,2, 2-tetramethy)-1,2-bis(cyclopentadienyl)disilane, (1,2-bis(cyclopentadienyl)ethane, and dimethyl (cyclopentadienyl)-1-(fluoren-1-yl)methane.

Preferred X" groups are selected from hydride, hydrocarbyl, silyl, germyl, halohydrocarbyl, halosilyl, silyl-hydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention corresponds to the preceding formula $Lp_lMX_mX'_nX''_p$, or a dimer thereof, wherein X is a divalent substituent of up to 50 non-hydrogen atoms that together with Lp forms a metallocycle with M.

Preferred divalent X substituents include groups containing up to 30 non-hydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention corresponds to the formula:

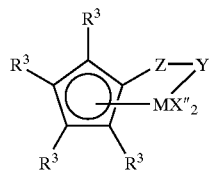

wherein:

M is titanium or zirconium, preferably titanium in the +2, +3, or +4 formal oxidation state;

R³ in each occurrence independently is selected from the group consisting of hydrogen, hydrocarbyl, silyl, germyl, cyano, halo and combinations thereof, said R³ having up to 20 non-hydrogen atoms, or adjacent R³ groups together form a divalent derivative (that is, a hydrocarbadiyl, siladiyl or germadiyl group) thereby forming a fused ring system, each X" is a halo, hydrocarbyl, hydrocarbyloxy or silyl group, said group having up to 20 non-hydrogen atoms, or two X" groups together form a neutral $C_{5-30}$ conjugated diene or a divalent derivative thereof;

Y is —O—, —S—, —NR*—, —PR*—; and

Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein R* is as previously defined.

Illustrative Group 4 metal complexes that may be employed in the practice of the present invention include:

cyclopentadienyltitaniumtrimethyl,
cyclopentadienyltitaniumtriethyl,
cyclopentadienyltitaniumtriisopropyl,
cyclopentadienyltitaniumtriphenyl,
cyclopentadienyltitaniumtribenzyl,
cyclopentadienyltitanium-2,4-dimethylpentadienyl,
cyclopentadienyltitanium-2,4-dimethylpentadienyl.triethylphosphine,
cyclopentadienyltitanium-2,4-dimethylpentadienyl.trimethylphosphine,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltitaniumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
pentamethylcyclopentadienyltitaniumdimethylchloride,
bis(η⁵-2,4-dimethylpentadienyl)titanium,
bis(η⁵-2,4-dimethylpentadienyl)titanium.trimethylphosphine,
bis(η⁵-2,4-dimethylpentadienyl)titanium.triethylphosphine,
octahydrofluorenyltitaniumtrimethyl,
tetrahydroindenyltitaniumtrimethyl,
tetrahydrofluorenyltitaniumtrimethyl,
(tert-butylamido)(1,1-dimethyl-2,3,4,9,10-η-1,4,5,6,7,8-hexahydronaphthalenyl)dimethylsilanetitaniumdimethyl, (tert-butylamido)(1,1,2,3-tetramethyl-2,3,4,9,10-η-1,4,5,6,7,8-hexahydronaphthalenyl) dimethylsilanetitaniumdimethyl,
(tert-butylamido)(tetramethyl-η$^5$-cyclopentadienyl) dimethylsilanetitanium dibenzyl,
(tert-butylamido)(tetramethyl-η$^5$-cyclopentadienyl) dimethylsilanetitanium dimethyl,
(tert-butylamido)(tetramethyl-η$^5$-cycopentadienyl)-1,2-ethanediyltitanium dimethyl,
(tert-butylamido)(tetramethyl-η$^5$-indenyl) dimethylsilanetitanium dimethyl,
(tert-butylamido)(tetramethyl-η$^5$-cyclopentadienyl) dimethylsilanetitanium (III) 2-(dimethylamino)benzyl;
(tert-butylamido)(tetramethyl-η$^5$-cyclopentadienyl) dimethylsilanetitanium (III) allyl,
(tert-butylamido)(tetramethyl-η$^5$-cyclopentadienyl) dimethylsilanetitanium (III) 2,4-dimethylpentadienyl,
(tert-butylamido)(tetramethyl-η$^5$-cyclopentadienyl) dimethylsilanetitanium (II) 1,4-diphenyl-1,3-butadiene,
(tert-butylamido)(tetramethyl-η$^5$-cyclopentadienyl) dimethylsilanetitanium (II) 1,3-pentadiene,
(tert-butylamido)(2-methylindenyl) dimethylsilanetitanium (II) 1,4-diphenyl-1,3-butadiene,
(tert-butylamido)(2-methylindenyl) dimethylsilanetitanium (II) 2,4-hexadiene,
(tert-butylamido)(2-methylindenyl) dimethylsilanetitanium (IV) 2,3-dimethyl-1,3-butadiene,
(tert-butylamido)(2-methylindenyl) dimethylsilanetitanium (IV) isoprene,
(tert-butylamido)(2-methylindenyl) dimethylsilanetitanium (IV) 1,3-butadiene,
(tert-butylamido)(2,3-dimethylindenyl) dimethylsilanetitanium (IV) 2,3-dimethyl-1,3-butadiene,
(tert-butylamido)(2,3-dimethylindenyl) dimethylsilanetitanium (IV) isoprene
(tert-butylamido)(2,3-dimethylindenyl) dimethylsilanetitanium (IV) dimethyl
(tert-butylamido)(2,3-dimethylindenyl) dimethylsilanetitanium (IV) dibenzyl
(tert-butylamido)(2,3-dimethylindenyl) dimethylsilanetitanium (IV) 1,3-butadiene,
(tert-butylamido)(2,3-dimethylindenyl) dimethylsilanetitanium (II) 1,3-pentadiene,
(tert-butylamido)(2,3-dimethylindenyl) dimethylsilanetitanium (II) 1,4-diphenyl-1,3-butadiene,
(tert-butylamido)(2-methylindenyl) dimethylsilanetitanium (II) 1,3-pentadiene,
(tert-butylamido)(2-methylindenyl) dimethylsilanetitanium (IV) dimethyl,
(tert-butylamido)(2-methylindenyl) dimethylsilanetitanium (IV) dibenzyl,
(tert-butylamido)(2-methyl-4-phenylindenyl) dimethylsilanetitanium (II) 1,4-diphenyl-1,3-butadiene,
(tert-butylamido)(2-methyl-4-phenylindenyl) dimethylsilanetitanium (II) 1,3-pentadiene,
(tert-butylamido)(2-methyl-4-phenylindenyl) dimethylsilanetitanium (II) 2,4-hexadiene,
(tert-butylamido) (tetramethyl-η$^5$-cyclopentadienyl) dimethylsilanetitanium (IV) 1,3-butadiene,
(tert-butylamido)(tetramethyl-η$^5$-cyclopentadienyl) dimethylsilanetitanium (IV) 2,3-dimethyl-1,3-butadiene,
(tert-butylamido)(tetramethyl-η$^5$-cyclopentadienyl) dimethylsilanetitanium (IV) isoprene,
(tert-butylamido)(tetramethyl-η$^5$-cyclopentadienyl) dimethyl- silanetitanium (II) 1,4-dibenzyl-1,3-butadiene,
(tert-butylamido)(tetramethyl-η$^5$-cyclopentadienyl) dimethylsilanetitanium (II) 2,4-hexadiene,
(tert-butylamido)(tetramethyl-η$^5$-cyclopentadienyl) dimethyl- silanetitanium (II) 3-methyl-1,3-pentadiene,
(tert-butylamido)(2,4-dimethylpentadien-3-yl) dimethylsilanetitaniumdimethyl,
(tert-butylamido)(6,6-dimethylcyclohexadienyl) dimethylsilanetitaniumdimethyl,
(tert-butylamido)(1,1-dimethyl-2,3,4,9,10-η-1,4,5,6,7,8-hexahydronaphthalen-4-yl) dimethylsilanetitaniumdimethyl,
(tert-butylamido)(1,1,2,3-tetramethyl-2,3,4,9,10-η-1,4,5,6,7,8-hexahydronaphthalen-4-yl) dimethylsilanetitaniumdimethyl
(tert-butylamido)(tetramethyl-η$^5$-cyclopentadienyl methylphenylsilanetitanium (IV) dimethyl,
(tert-butylamido)(tetramethyl-η$^5$-cyclopentadienyl methylphenylsilanetitanium (II) 1,4-diphenyl-1,3-butadiene,
1-(tert-butylamido)-2-(tetramethyl-η$^5$-cyclopentadienyl) ethanediyltitanium (IV) dimethyl,
1-(tert-butylamido)-2-(tetramethyl-η$^5$-cyclopentadienyl) ethanediyl- titanium (11) 1,4-diphenyl-1,3-butadiene,
(tert-butylamido)(3-(N-pyrrolidinyl)indenyl) dimethylsilanetitanium (IV) 2,3-dimethyl-1,3-butadiene,
(tert-butylamido)(3-(N-pyrrolidinyl)indenyl) dimethylsilanetitanium (IV) isoprene
(tert-butylamido)(3-(N-pyrrolidinyl)indenyl) dimethylsilanetitanium (IV) dimethyl
(tert-butylamido)(3-(N-pyrrolidinyl)indenyl) dimethylsilanetitanium (IV) dibenzyl
(tert-butylamido)(3-(N-pyrrolidinyl)indenyl) dimethylsilanetitanium (IV) 1,3-butadiene,
(tert-butylamido)(3-(N-pyrrolidinyl)indenyl) dimethylsilanetitanium (II) 1,3-pentadiene,
(tert-butylamido) (3-(N-pyrrolidinyl)indenyl) dimethylsilanetitanium (II) 1,4-diphenyl-1,3-butadiene, and
(tert-butylamido)(3-N-pyridinylindenyl) dimethylsilanetitanium (II) 2,4-hexadiene.

Complexes containing two Lp groups including bridged complexes suitable for use in the present invention include:
bis(cyclopentadienyl)zirconiumdimethyl,
bis(cyclopentadienyl)zirconium dibenzyl,
bis(cyclopentadienyl)zirconium methyl benzyl,
bis(cyclopentadienyl)zirconium methyl phenyl,
bis(cyclopentadienyl)zirconiumdiphenyl,
bis(cyclopentadienyi)titanium-allyl,
bis(cyclopentadienyl)zirconiummethylmethoxide,
bis(cyclopentadienylzirconiummethylchloride,
bis(pentamethylcyclopentadienyl)zirconiumdimethyl, bis(pentamethylcyclopentadienyl)titaniumdimethyl,
bis(indenyl)zirconiumdimethyl,
indenylfluorenylzirconiumdimethyl,
bis(indenyl)zirconiummethyl(2-(dimethylamino)benzyl),
bis(indenyl)zirconiummethyltrimethylsilyl,
bis(tetrahydroindenyl)zirconiummethyltrimethylsilyl,
bis(pentamethylcyclopentadienyl)zirconiummethylbenzyl,
bis(pentamethylcyclopentadienyl)zirconiumdibenzyl,
bis(pentamethylcyclopentadienyl)zirconiummethylmethoxide,
bis(pentamethylcyclopentadienyl)zirconiummethylchloride,
bis(methylethylcyclopentadienyl)zirconiumdimethyl,
bis(butylcyclopentadienyl)zirconiumdibenzyl,
bis(t-butylcyclopentadienyl)zirconiumdimethyl,
bis(ethyltetramethylcyclopentadienyl)zirconiumdimethyl,
bis(methylpropylcyclopentadienyl)zirconiumdibenzyl,
bis(trimethylsilylcyclopentadienyl)zirconiumdibenzyl,
dimethylsilyi-bis(cyclopentadienyl)zirconiumdimethyl,
dimethylsilyl-bis(tetramethylcyclopentadienyl)titanium (III) allyl
dimethylsilyl-bis(t-butylcyclopentadienyl)hafnium dimethyl,
dimethylsilyl-bis(2-methyl-4-phenylindenyl)hafnium dimethyl,
(methylene-bis(tetramethylcyclopentadienyl)titanium (III) 2-(dimethylamino)benzyl,
(methylene-bis(n-butylcyclopentadienyl)titanium(III) 2-(dimethylamino)benzyl,
dimethylsilyl-bis(indenyl)zirconiumbenzylchloride,
dimethylsilyl-bis(2-methylindenyl)zirconiumdimethyl,
dimethylsilyl-bis(2-methyl-4-phenylindenyl)zirconiumdimethyl,
dimethylsilyl-bis(2-methylindenyl)zirconium-1,4-diphenyl-1,3-butadiene,
dimethylsilyl-bis(2-methyl-4-phenylindenyl)zirconium (II) 1,4-diphenyl-1,3-butadiene,
dimethylsilyl-bis(tetrahydroindenyl)zirconiom(II) 1,4-diphenyl-1,3-butadiene,
dimethylsilyl-bis(fluorenyl)zirconiummethylchloride,
dimethylsilyl-bis(tetrahydrofluorenyl)zirconium bis (trimethylsilyl),
(isopropylidene)(cyclopentadienyl)(fluorenyl) zirconiumdibenzyl, and
dimethylsilyl(tetramethylcyclopentadienyl) (fluorenyl) zirconium dimethyl.

Other catalysts, especially catalysts containing other Group 4 metals, will, of course, be apparent to those skilled in the art. Most highly preferred metal complexes for use herein are the following metal complexes:

(t-butylamido)dimethyl(tetramethylcyclopentadienyl) silanetitanium dimethyl, (t-butylamido)dimethyl (tetramethylcyclopentadienyl)silanetitanium (II) 1,3-pentadiene, (t-butylamido)dimethyl (tetramethylcyclopentadienyl)silanetitanium (II) 1,4 diphenyl-1,3-butadiene, (cyclohexylamido)dimethyl (tetramethylcyclopentadienyl)silanetitanium dimethyl, cyclohexylamido)oimethyl (tetramethylcyclopentadienyl)silanetitanium (II) 1,3-pentadiene, cyclohexylamido)dimethyl (tetramethylcyclopentadienyl)silanetitanium (II) 1,4 diphenyl-1,3-butadiene, (cyclododecylamido)dimethyl (tetramethylcyclopentadienyl)silanetitanium dimethyl, (cyclododecylamido)dimethyl (tetramethylcyclopentadienyl)silanetitanium (II) 1,3-pentadiene, (cyclododecylamido)dimethyl (tetramethylcyclopentadienyl)silanetitanium (II) 1,4 diphenyl-1,3-butadiene, (t-butylamido)dimethyl(2-methyl-s-indacen-1-yl) silanetitanium dimethyl, (t-butylamido)dimethyl(2-methyl-s-indacen-1- yl) silanetitanium (II) 1,3-pentadiene, (t-butylamido)dimethyl(2-methyl-s-indacen-1-yl)silanetitanium(II) 1,4 diphenyl-1,3-butadiene, (cyclohexylamido)dimethyl(2-methyl-s-indacen-1-yl) silanetitanium dimethyl, cyclohexylamido)dimethyl(2-methyl-s-indacen-1-yl)silanetitanium(II) 1,3-pentadiene, cyclohexylamido)dimethyl(2-methyl-s-indacen-1-yl)silanetitanium(II) 1,4 diphenyl-1,3-butadiene, (cyclododecylamido)dimethyl(2-methyl-s-indacen-1-yl) silanetitanium dimethyl, (cyclododecylamido)dimethyl (2-methyl-s-indacen-1-yl)silanetitanium(II) 1,3-pentadiene, (cyclododecylamido)di'methyl(2-methyl-s-indacen-1-yl)silanetitanium(II) 1,4 diphenyl-1,3-butadiene, (t-butylamido)dimethyl(3,4-(cyclopenta(l)phenanthren-1-yl)silanetitanium dimethyl,
(t-butylamido)dimethyl(3,4-(cyclopenta(l)phenanthren-1-yl)silanetitanium(II) 1,3-pentadiene,
(t-butylamido)dimethyl(3,4-(cyclopenta(l)phenanthren-1-yl)silanetitanium(II) 1,4 diphenyl-1,3-butadiene, (cyclohexylamido)dimethyl(3,4-(cyclopenta(l) phenanthren-1-yl)silanetitanium dimethyl, cyclohexylamido)dimethyl(3,4-(cyclopenta(l) phenanthren-1-yl)silanetitanium(II) 1,3-pentadiene, cyclohexylamido)dimethyl(3,4-(cyclopenta(l) phenanthren-1-yl)silanetitanium(II) 1,4 diphenyl-1,3-butadiene, (cyclododecylamido)dimethyl(3,4-(cyclopenta(l) phenanthren-1-yl)silanetitanium dimethyl, (cyclododecylamido)dimethyl(3,4-(cyclopenta(l) phenanthren-1-yl)silanetitanium(II) 1,3-pentadiene, (cyclododecylamido)dimethyl(3,4-(cyclopenta(l) phenanthren-1-yl)silanetitanium(II) 1,4 diphenyl-1,3-butadiene, (t-butylamido)dimethyl(2-methyl-4-phenylinden-1-yl) silanetitanium dimethyl, (t-butylamido)dimethyl(2-methyl-4-phenylinden-1-yl)silanetitanium(II) 1,3-pentadiene, (t-butylamido)dimethyl(2-methyl-4-phenylinden-1-yl)silanetitanium(II) 1,4 diphenyl-1,3-butadiene, (cyclohexylamido)dimethyl(2-methyl-4-phenylinden-1-yl)silanetitanium dimethyl, cyclohexylamido)dimethyl (2-methyl-4-phenylinden-1-yl)silanetitanium(II) 1,3-pentadiene, cyclohexylamido)dimethyl(2-methyl-4-phenylinden-1-yl)silanetitanium(II) 1,4 diphenyl-1,3-butadiene, (cyclododecylamido)dimethyl(2-methyl-4-phenylinden-1-yl)silanetitanium dimethyl, (cyclododecylamido) dimethyl(2-methyl-4-phenylinden-1-yl)silanetitanium (II) 1,3-pentadiene, (cyclododecylamido)dimethyl(2-methyl-4-phenylinden-1-yl)silanetitanium(II) 1,4 diphenyl-1,3-butadiene,
(t-butylamido)dimethyl(2-methyl-4-phenylinden-1-yl)silanetitanium dimethyl, (t-butylamido)dimethyl(2-methyl-4-phenylinden-1-yl)silanetitanium (II) 1,3-pentadiene, (t-butylamido)dimethyl(2-methyl-4-phenylinden-1-yl)silanetitanium (II) 1,4 diphenyl-1,3-butadiene,
(cyclohexylamido)dimethyl(2-methyl-4-phenylinden-1-yl)silanetitanium dimethyl, cyclohexylamido)dimethyl(2-methyl-4-phenylinden-1-yl)silanetitanium(II) 1,3-pentadiene, cyclohexylamido)dimethyl(2-methyl-4-phenylinden-1-yl)silanetitanium(II) 1,4 diphenyl-1,3-butadiene,
(cyclododecylamido)dimethyl(2-methyl-4-phenylinden-1-yl)silanetitanium dimethyl, (cyclododecylamido)dimethyl(2-methyl-4-phenylinden-1-yl)silanetitanium (II) 1,3-pentadiene,
(cyclododecylamido)dimethyl(2-methyl-4-phenylinden-1-yl)silanetitanium(II) 1,4 diphenyl-1,3-butadiene,
(t-butylamido)dimethyl(3-(1-pyrrolidinyl)inden-1-yl)silanetitanium dimethyl, (t-butylamido)dimethyl(3-(1-pyrrolidinyl)inden-1-yl)silanetitanium(II) 1,3-pentadiene, (t-butylamido)dimethyl(3-(1-pyrrolidinyl)inden-1-yl)silanetitanium(II) 1,4 diphenyl-1,3-butadiene,
(cyclohexylamido)dimethyl(3-(1-pyrrolidinyl)inden-1-yl)silanetitanium dimethyl, cyclohexylamido)dimethyl(3-(1-pyrrolidinyl)inden-1-yl)silanetitanium(II) 1,3-pentadiene, cyclohexylamido)dimethyl(3-(1-pyrrolidinyl)inden-1-yl)silanetitanium(II) 1,4 diphenyl-1,3-butadiene,
(cyclododecylamido)dimethyl(3-(1-pyrrolidinyl)inden-1-yl)silanetitanium dimethyl (cyclododecylamido)dimethyl(3-(1-pyrrolidinyl)inden-1-yl)silanetitanium (II) 1,3-pentadiene,
(cyclododecylamido)dimethyl(3-(1-pyrrolidinyl)inden-1-yl)silanetitanium(II) 1,4 diphenyl-1,3-butadiene,
(t-butylamido)dimethyl(3-(1-pyrrolidinyl)inden-1-yl)silanetitanium dimethyl, (t-butylamido)dimethyl(3-(1-pyrrolidinyl)inden-1-yl)silanetitanium(II) 1,3-pentadiene, (t-butylamido)dimethyl(3-(1-pyrrolidinyl)inden-1-yl)silanetitanium(II) 1,4 diphenyl-1,3-butadiene,
(cyclohexylamido)dimethyl(3-(1-pyrrolidinyl)inden-1-yl)silanetitanium dimethyl, cyclohexylamido)dimethyl(3-(1-pyrrolidinyl)inden-1-yl)silanetitanium(II) 1,3-pentadiene, cyclohexylamido)dimethyl(3-(1-pyrrolidinyl)inden-1-yl)silanetitanium(II) 1,4 diphenyl-1,3-butadiene,
(cyclododecylamido)dimethyl(3-(1-pyrrolidinyl)inden-1-yl)silanetitanium dimethyl, (cyclododecylamido)dimethyl(3-(1-pyrrolidinyl)inden-1-yl)silanetitanium (II) 1,3-pentadiene,
(cyclododecylamido)dimethyl(3-(1-pyrrolidinyl)inden-1-yl)silanetitanium(II) 1,4 diphenyl-1,3-butadiene,
1,2-ethanebis(inden-1-yl)zirconium dimethyl, 1,2-ethanebis(inden-1-yl)zirconiume(II) 1,3-pentadiene, 1,2-ethanebis(inden-1-yl)zirconium(II) 1,4 diphenyl-1,3-butadiene, 1,2-ethanebis(2-methyl-4-phenylinden-1-yl)zirconium dimethyl, 1,2-ethanebis(2-methyl-4-phenylinden-1-yl)zirconium(II) 1,3-pentadiene, 1,2-ethanebis(2-methyl-4-phenylinden-1-yl)zirconium(II) 1,4 diphenyl-1,3-butadiene,
dimethylsilanebis(inden-1-yl)zirconium dimethyl, dimethylsilanebis(inden-1-yl)zirconium(II) 1,3-pentadiene, dimethylsilanebis(inden-1-yl)zirconium (II) 1,4 diphenyl-1,3-butadiene, dimethylsilanebis(2-methyl-4-phenylinden-1-yl)zirconium dimethyl, dimethylsilanebis(2-methyl-4-phenylinden-1-yl)zirconium(II) 1,3-pentadiene, and dimethylsilanebis(2-methyl-4-phenylinden-1-yl)zirconium(II) 1,4 diphenyl-1,3-butadiene.

Suitable supports, component A), for use in the present invention include any inert, solid, finely comminuted or particulated substance. Examples include metal oxides, metal nitrides, metal carbides, metal silicates, metal fluorosilicates, metalloid carbides, metalloid nitrides, mixtures of the foregoing, and synthetic hydrocarbon or silicone based polymers. As used herein, the term "inert" means that the support does not interfere with the desired polymerization reaction in a detrimental manner. However, the support may interact with the catalyst components, such as by reaction to bind one aor more of the individual components to the surface of the support without detrimentally affecting the components desired physical or chemical properties in an addition polymerization. Preferred supports include silica, aluminosilicates, clays, alumina, titanates, silicon carbide, magnesium silicates and magnesium fluorosilicates, especially such materials that have been treated in one or more ways to remove detrimental reactive functionality therefrom. A most preferred support material is silica that has been thoroughly dried to remove water and treated with a silane or metal hydrocarbyl compound to remove or partially remove reactive functional groups, primarily hydroxyl groups.

The support is preferably treated to remove water and physisorbed oxygen, or other contaminants prior to use herein. Such treatment may be accomplished by any suitable means known in the art. Suitable techniques include heating optionally while exposing the substrate to reduced pressure. In addition, the support may be contacted with an agent such as a metal alkyl, particularly an aluminum trialkyl having from 1 to 6 carbons in each alkyl group, an alumoxane, or a reactive silane compound, to react with or "cap" some or substantially all deleterious functional groups, such as hydroxy groups on the surface of the support or otherwise modify the chemical properties of the support, prior to use herein.

The supported polymerization catalysts are prepared by contacting the metal complex and activator compound with the support in any order and by the use of any suitable technique. In particular, the catalyst and activator may be deposited from a liquid onto the surface of the support by spraying or slurrying a solution or suspension of the metal complex and activator compounds, in combination or separately in any order, and optionally repeated. Thereafter or concurrently therewith, most or all of the residual solvent or diluent is desirably removed by evaporation, optionally under reduced pressure or at elevated temperatures.

The supported polymerization catalysts of the invention may additionally include an organometallic compound of up to 20 atoms not counting hydrogen, wherein the metal is selected from groups 12–14 of the Periodic Table of the Elements, preferably aluminum. Examples include an oligomeric or polymeric alumoxane compound, a tri (hydrocarbyl)aluminum compound, a di(hydrocarbyl)(hydrocarbyloxy)aluminum compound, a di(hydrocarbyl)(dihydrocarbylamido)aluminum compound, a bis(dihydrocarbyl-amido)(hydrocarbyl)aluminum compound, a di(hydrocarbyl)amido-(disilyl)aluminum compound, a di(hydrocarbyl)amido(hydrocarbyl)(silyl)aluminum compound, a bis(dihydrocarbylamido)(silyl)aluminum compound, or a mixture of the foregoing compounds, having from 1 to 20 non-hydrogen atoms in each hydrocarbyl, hydrocarbyloxy, or silyl group. These compounds are usefully employed for their beneficial ability to scavenge impurities such as oxygen, water, and aldehydes from the polymerization mixture as well as to react with residual hydroxyl or other moieties of the support in order to prevent subsequent detrimental reaction with the catalyst components. They may be added to the supported catalyst on the surface of the support or included in the reaction mixture in the slurry reactor.

Preferred aluminum compounds include $C_{1-20}$ trialkyl aluminum compounds, especially those wherein the alkyl groups are dialkyl(aryloxy)aluminum compounds containing from 1–6 carbons in the alkyl group and from 6 to 18 carbons in the aryl group (especially (3,5-di(t-butyl)-4-methylphenoxy)diisobutylaluminum), methylalumoxane, and isobutyl- modified methylalumoxane. The molar ratio of metal complex to aluminum compound is preferably from 1:10,000 to 1000:1, more preferably from 1:5000 to 100:1, most preferably from 1:100 to 100:1.

In a preferred embodiment, the organometallic compound is a trihydrocarbyl aluminum compound having from 1 to 6 carbons in each hydrocarbyl group, especially a trialkyl aluminum compound, preferably trimethyl aluminum or triethyl aluminum, that is combined with the support that has been previously thoroughly dried. Desirably, the quantity of organometallic compound employed is less than a stoichiometric quantity based on the sum of any remaining water plus the quantity of residual hydroxyl groups on the surface of the support, preferably in a molar ratio from 0.5:1.0 to 0.99:1.0, more preferably from 0.85:1.0 to 0.95:1.0 based on this total of water+residual hydroxyl content (referred to as total hydroxyl content). The value of such total hydroxyl content may be determined by titration with a Lewis acid such as a trialkylaluminum compound.

Such a pretreated support material is believed to contain sufficient residual hydroxyl functionality to react with Lewis acid groups of the activator compound thereby chemically attaching the activator compound to the substrate. Such chemically attached activator compound containing catalysts are particularly adapted for use in slurry polymerizations due to the fact that the active catalyst species resists being washed from the support by the reaction medium or diluent under use conditions. Certain of the activators may be more soluble in organic liquids than others, due for example to the presence of more oliophillic groups in the molecule. For example, long chain alkyl substituted imidazolide salts such as the undecyl- substituted imidazolides are somewhat more soluble in hydrocarbons compared to the corresponding unsubstituted salts. Such compounds form more hydrocarbon resistant supported catalyst compositions, which accordingly are more suited for use under slurry polymerization conditions, when deposited onto substrates containing residual hydroxyl functionality.

Preferred support materials in this embodiment of the invention are finely particulated materials that remain solids under conditions of preparation and use and that do not interfere with subsequent polymerizations or other uses of the composition of the invention. Suitable support materials especially include particulated metal oxides, oxides of silicon or germanium, polymers, and mixtures thereof. Examples include alumina, silica, aluminosilicates, clay, and particulated polyolefins. Suitable volume average particle sizes of the support are from 1 to 1000 $\mu M$, preferably from 10 to 100 $\mu M$. Preferably, the support material has a porosity of from 0.2 to 1.5 cubic centimeters per gram (cc/g), more preferably from 0.3 to 1.2 cc/g, and most preferably from 0.5 to 1.0 cc/g, determined by the BET nitrogen technique. Most desired supports are particulated silica, that has been thoroughly dried, suitably by heating to 200 to 900° C. for from 10 minutes to 2 days. The silica is desirably then treated prior to use to further reduce surface hydroxyl groups thereon, or to introduce more reactive functionality than the available hydroxyl functionality for subsequent reaction with the activator compound. Suitable treatments include reaction with a tri($C_{1-10}$ alkyl)silylhalide, hexa($C_{1-10}$ alkyl) disilazane, tri($C_{1-10}$ alkyl)aluminum, or similar reactive compound, preferably by contacting the support and a hydrocarbon solution of the reactive compound.

In a preferred embodiment, silica is reacted with a tri($C_{1-10}$alkyl)aluminum, most preferably, trimethylaluminum, triethylaluminum, triisopropylaluminum or triisobutylaluminum, in an amount from 0.1 to 100, more preferably 0.2 to 10 mmole aluminum/g silica, and thereafter contacted with the above activator composition, or a solution thereof, in a quantity sufficient to provide an active supported cocatalyst for olefin polymerization according to the invention.

The activator and particulated support material may be combined and reacted in any aliphatic, alicyclic or aromatic liquid diluent, or solvent, or mixture thereof, or reacted in solid, neat form. Preferred diluents or solvents are $C_{4-10}$ hydrocarbons and mixtures thereof, including hexane, heptane, cyclohexane, and mixed fractions such as Isopar™ E, available from Exxon Chemicals Inc. Preferred contacting times are at least one hour, preferably at least 90 minutes, at a temperature from 0 to 75° C., preferably from 20 to 50° C., most preferably from 25 to 35° C. Desirably, the contacting is also done prior to addition of a metal complex catalyst, such as a metallocene, to the mixture or either component separately, in order to avoid formation of further derivatives and multiple metal exchange products having reduced catalytic effectiveness. After contacting of the support and activator, the reaction mixture may be purified to remove byproducts, if any, by any suitable technique. Alternatively, but less desirably, a Group 3–10 metal complex catalyst may first be combined with the reaction mixture prior to removing byproducts.

Active supported catalyst compositions are prepared by contacting a metal complex or a mixture of metal complexes to be activated with the above disclosed support. Any suitable means for incorporating the metal complex onto the surface of a support (including the interstices thereof) may be used, including dispersing or dissolving the same in a liquid and contacting the mixture or solution with the support by slurrying, impregnating, spraying, or coating and thereafter removing the liquid, or by combining the metal complex and support material in dry or paste form and intimately contacting the mixture, thereafter forming a dried, particulated product.

Suitable metal complexes for use in combination with the foregoing cocatalysts include any complex of a metal of Groups 3–10 of the Periodic Table of the Elements capable of being activated to polymerize addition polymerizable compounds, especially olefins by the present activators.

The activator compound used in the present invention are capable of activating a wide variety of metal complexes. Moreover, the cocatalysts can be optimized in their ability to activate different metal complexes through combination of anions, Z*, having Lewis base sites of varying base strength, and Lewis acids, J*, having varying acidity. For example, catalyst compositions having long catalyst lifetimes and less exothermic reactions have anions containing less basic Lewis base sites in combination with less acidic Lewis acids. Such catalysts may be highly desirable for use in gas phase polymerizations where adequate heat removal may be critical to success.

The equivalent ratio of catalyst:cocatalyst (calculated based on quantity of metal in the catalyst and anionic charges on the cocatalyst) employed preferably ranges from 1:10 to 10:1, more preferably from 1:5 to 2:1, most preferably from 1:4 to 1:1. Mixtures of activator compounds may also be employed if desired.

Suitable addition polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1,1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1,1-hexene, 1-octene, and combinations of ethylene and/or propene with one or more of such other alpha-olefins. Other preferred monomers include styrene, halo- or alkyl substituted styrenes, vinylbenzocyclobutene, 1,4-hexadiene, dicyclopentadiene, ethylidene norbornene, and 1,7-octadiene. Mixtures of the above-mentioned monomers may also be employed.

In general, the polymerization may be accomplished at conditions well known in the prior art for Ziegler-Natta or Kaminsky-Sinn type polymerization reactions operating under slurry process conditions. Preferred conditions are semibatch or continuous process conditions operating at polymerization temperatures of 25 to 100° C., preferably from 30 to 80° C. Preferred polymerization pressures are from 0.1 Mpa to 30 Mpa, preferably from 1 to 10 Mpa.

Preferably, the polymerization is conducted in the presence of an aliphatic or alicyclic liquid diluent at a temperature such that the polymer precipitates from solution thereby forming a particulated solid. By the term "continuous polymerization" is meant that at least the product of the polymerization is continuously removed from the reaction mixture. Preferably one or more reactants are also continuously added to the polymerization mixture during the polymerization. Examples of suitable aliphatic or alicyclic liquid diluents include straight and branched-chain $C_{4-12}$ hydrocarbons and mixtures thereof; alicyclic hydrocarbons such as cyclohexane, cycloheptane, methylcyclohexane, methylcycloheptane, and mixtures thereof; and perfluorinated hydrocarbons such as perfluorinated $C_{4-10}$ alkanes, and the like. Suitable diluents also include aromatic hydrocarbons (particularly for use with aromatic α-olefins such as styrene or ring alkyl-substituted styrenes) including toluene, ethylbenzene or xylene, as well as liquid olefins (which may act as monomers or comonomers) including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable. The foregoing diluents may also be advantageously employed during the synthesis of the metal complexes and catalyst activators and formation of the supported catalysts of the present invention as well.

In most polymerization reactions the molar ratio of catalyst to polymerizable compounds employed is from $10^{-12}$:1 to $10^{-1}$:1, more preferably from $10^{-12}$:1 to $10^{-5}$:1.

Molecular weight control agents can be used in combination with the present cocatalysts. Examples of such molecular weight control agents include hydrogen, trialkyl aluminum compounds or other known chain transfer agents. Desirably the polymer obtained from the reactor has a high bulk density, preferably greater than 0.3 g/ml, more preferably greater than 0.35 g/ml. The catalyst are also advantageously employed in a process that produces little or no reactor fouling due to deposition of solid polymer onto surfaces within the reactor.

The catalysts are especially suited for use in the homopolymerization and copolymerization of ethylene and propylene, and the copolymerization of ethylene with higher alpha olefins such as, for example, 1-butene, 1-hexene, 4-methyl-1-pentene for the manufacture of high density polyethylene (HDPE), medium density polyethylene (MDPE), linear low density polyethylene (LLDPE,), low density polyethylene (LDPE), and polypropylene.

The gas phase polymerization process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate or fluidisation grid, by a flow of fluidisation gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having about 3 to about 8, preferably 4 to 6, carbon atoms. In the case that the monomer or comonomer itself is a volatile liquid, or can be condensed to provide such a liquid this can be suitably be fed to the bed to provide an evaporative cooling effect. Examples of olefin monomers which can be employed in this manner are olefins containing from about 3 to about eight, preferably from 3 to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5,352,749. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032.

The polymerization reaction occurring in the gas fluidized bed is catalyzed by the continuous or semi-continuous addition of catalyst. Such catalyst can be supported on an inorganic or organic support material if desired. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerization of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with inert gas or nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. All manipulation of air sensitive materials was performed in a nitrogen filled glove box or on a high vacuum line using standard Shlenk techniques.

A) Silica Treatment

A1 Silica (Grace-Davison 948, available from Grace-Davison division of W.R. Grace) was dehydrated at 250° C. for 3 hours in air. Then, the silica was slurried in hexane and the resulting mixture treated with a 1.00 M solution of triethylaluminum (TEA) in hexane in an amount to provide 1 mmol TEA/g silica. The mixture was agitated for 30 minutes and then the solids were isolated by filtration, washed twice with hexane and dried under reduced pressure. Because less than a stoichiometric amount of triethylaluminum compared to the quantity of reactive sites on the silica was employed, residual hydroxyl functionality remained on the surface of the silica.

A2 Silica (Grace-Davison 948, available from Grace-Davison division of W.R. Grace) was dehydrated at 250° C. for 3 hours in air. Then, the silica was slurried in hexane and the resulting mixture treated with a 1.00 M solution of triethylaluminum (TEA) in hexane in an amount to provide 2.1 mmol TEA/g silica. The mixture was agitated for 30 minutes and then the solids were isolated by filtration, washed twice with hexane and dried under reduced pressure. Because more than a stoichiometric amount of triethylaluminum compared to the quantity of reactive sites on the silica was employed, the resulting support had substantially no residual hydroxyl functionality remaining on the surface of the silica.

A3 Silica (surface area 305 m$^2$/g, pore volume 1.49 ml/g) was dehydrated at 250° C. for 3 hours in air. Then the silica was slurried in hexane and treated with a 1.00 M solution of triethylaluminum in hexane in an amount to provide 2.5 mmol TEA/g silica.

A4 Silica (Crosfield ES-70, available from Crosfield Limited) was dehydrated at 250° C. for 3 hours in air. Then, the silica was slurried in hexane and the resulting mixture treated with a 1.00 M solution of triethylaluminum (TEA) in hexane in an amount to provide 2.5 mmol TEA/g silica. The mixture was agitated for 30 minutes and then the solids were isolated by filtration, washed twice with hexane and dried under reduced pressure.

A5 Silica (Grace-Davison 948, available from Grace-Davison division of W.R. Grace) was dehydrated at 250° C. for 3 hours in air. Then, the silica was slurried in hexane and the resulting mixture treated with a 1.00 M solution of triethylaluminum (TEA) in hexane in an amount to provide 2.5 mmol TEA/g silica. The mixture was agitated for 30 minutes and then the solids were isolated by filtration, washed twice with hexane and dried under reduced pressure.

A6 Silica (Crosfield ES-70, available from Crosfield Limited) was dehydrated at 500° C. for 3 hours in air. Then, the silica was slurried in hexane and the resulting mixture treated with a 1.00 M solution of triethylaluminum (TEA) in hexane in an amount to provide 2.5 mmol TEA/g silica. The mixture was agitated for 30 minutes and then the solids were isolated by filtration, washed twice with hexane and dried under reduced pressure.

A7 Silica (Grace-Davison 948, available from Grace-Davison division of W.R. Grace) was dehydrated at 250° C. for 4 hours in air. Then, the silica was slurried in hexane and the resulting mixture treated with a 1.00 M solution of triethylaluminum (TEA) in hexane in an amount to provide 1.5 mmol TEA/g silica. The mixture was agitated for 30 minutes and then the solids were isolated by filtration, washed once with toluene and once with hexane and dried under reduced pressure.

A8 Silica (surface area 527 m$^2$/g, pore volume 1.65 ml/g) was dehydrated at 250° C. for 3 hours in air. Then the silica was slurried in hexane and treated with a 1.00 M solution of triethylaluminum in hexane in an amount to provide 2.5 mmol TEA/g silica.

B) Metal Complex Preparation

B1 (t-butylamido)dimethyl(tetramethylcyclopentadienyl) silanetitanium (II) 1,3-pentadiene prepared substantially as disclosed in U.S. Pat. No. 5,470,993.

B2 rac-dimethylsilane bis($\eta^5$-2-methyl-4-phenylinden-1-yl)zirconium (II) 1,4-diphenyl-1,3-butadiene prepared substantially as disclosed in U.S. Pat. No. 5,616,664.

B3 rac-bis(N,N-diisopropylamidoborane bis($\eta^5$-2-methyl-4-phenylinden-1-yl)-zirconium (II) 1,4-diphenyl-1,3-butadiene prepared substantially as disclosed in WO99/20538 (U.S. Ser. No. 9/383,996, filed Aug. 26, 1999).

B4 rac-bis(N,N-dimethylamidoborane bis($\eta^5$-2-methyl-4-phenylinden-1-yl)zirconium (II) 1,4-diphenyl-1,3-butadiene prepared substantially as disclosed in WO99/20538 (U.S. Ser. No. 9/383,996, filed Aug. 26, 1999).

C) Activator Preparations

C1 di($C_{14-18}$ Alkyl)methylammonium 1,3-bis(tris(Pentafluorophenyl)alumane)-2-undecylimidazolide ([($C_{18}H_{37}$)$_2$CH$_3$NH][(($C_6F_5$)$_3$Al)$_2$C$_3$H$_3$N$_2$C$_{11}$H$_{23}$])

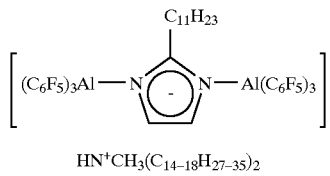

Undecylimidazole (0.267g, 1.20 mmol), tris(pentafluorophenyl)alumane (1.27 g, 2.40 mmol) and di($C_{14-18}$ alkyl)methylamine (Armeen™ M2HT0 available from Akzo Nobel, 0.64 g, 1.20 mmol) were placed in a 50 mL flask, taken up in 10 mL of mixed alkanes and refluxed under argon for 4.5 hours. The volatiles were then stripped under vacuum, giving 2.18 g of viscous beige oil (100 percent yield).

C2 di($C_{14-18}$ Alkyl)methylammonium 1,3-bis(tris(Pentafluorophenyl)alumane)-imidazolide ([($C_{14-18}H_{27-35}$)$_2$CH$_3$NH][(($C_6F_5$)$_3$Al)$_2$C$_3$H$_4$N$_2$

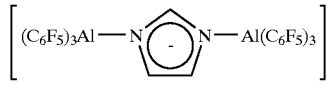

Imidazole (0.057 g, 0.83 mmol), tris(pentafluorophenyl)alumane (diethyletherate) (1.00 g, 1.66 mmol) and di($C_{14-18}$ alkyl)methylamine (Armeen™ M2HT0 available from Akzo Nobel, 0.445 g, 0.83 mmol) were placed in a 120 ml glass bottle. Toluene (40 ml) was added and the mixture was stirred for 16 hours. A condenser was added and the reaction mixture was heated to reflux temperature for 8 hours. The mixture was then cooled and concentrated to about 20 ml. The product's identity was confirmed by $^1$H and $^{19}$F NMR spectroscopy.

C3 di($C_{14-18}$ Alkyl)methylammonium 1,3-bis(tris(Pentafluorophenyl)borane)-4,5-diphenylimidazolide ([($C_{14-18}H_{27-35}$)$_2$CH$_3$NH][(($C_6F_5$)$_3$Al)$_2$C$_{15}$H$_{14}$N$_2$

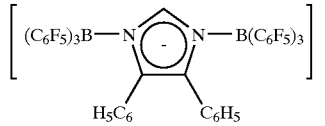

The preparation of C2 was substantially repeated using 4,5-diphenyl imidazole in place of imidazole and tris(pentafluorophenyl)borane in place of tris(pentafluorophenyl)aluminum.

C4 di($C_{14-18}$ Alkyl)methylammonium 1,3-bis(tris(Pentafluorophenyl)borane)-4,5-dichloroimidazolide

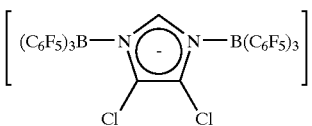
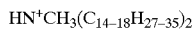

The preparation of C3 was substantially repeated using 4,5-dichloroimidazole in place of 4,5-diphenylimidazole.

C5 di($C_{14-18}$ Alkyl)methylammonium 1,3-bis(tris(Pentafluorophenyl)borane)-4,5-dichloroimidazolide

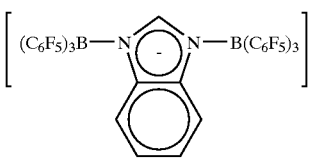
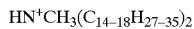

The preparation of C3 was substantially repeated using 4,5-benzimidazole in place of 4,5-diphenylimidazole.

C6 di($C_{14-18}$ Alkyl)methylammonium 1,3-bis(tris(Pentafluorophenyl)alumane)-triazolide

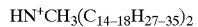

The preparation of C2 was substantially repeated using triazole in place of imidazole.

Example 1

The Components for This Supported Catalyst Were A1, B1 and C1

The silica (A1) was added to hexane (20 ml) and the mixture agitated for 15 minutes. Then, 5 ml of a 0.1 M solution of the activator (C1) in hexane was added and the resulting mixture agitated a further two hours. The slurry was then filtered, washed with two 10 ml portions of toluene and then two 10 ml portions of hexane, and dried under reduced pressure. 1 g Of this solid was slurried in 10 ml of hexane and 0.25 ml of a 0.2 M solution of the metal complex (B1) in mixed alkanes was added. The mixture was agitated for two hours, filtered, washed with two 10 ml portions of toluene and then two 10 ml portions of hexane, and dried under reduced pressure to yield the supported catalyst as a green-brown colored solid.

Polymerization

Slurry Ethylene Homopolymerization

A stirred 4.0 L reactor was charged with 1800 g of hexane and heated to the reaction temperature of 70° C. Ethylene was added to the reactor in an amount sufficient to bring the total pressure to the desired operating level of 1.3 Mpa (190 psi). 0.59 g Of the above described supported catalyst from Example 1 was then added to the reactor using nitrogen pressure. The reactor pressure was kept essentially constant by continually feeding ethylene on demand during the polymerization run while maintaining the reactor temperature at 70° C. with a cooling jacket. After 30 minutes, the ethylene flow was discontinued, the reactor was vented, and the contents of the reactor were transferred to a sample pan. Liquid was removed under reduced pressure leaving 25.7 g of free flowing polyethylene powder having a bulk density of 0.366 g/cm$^3$ and an average particle size of 267 micron. Under comparable conditions a supported catalyst prepared from silica that had been treated with TEA in an amount of 2.1 mmol/g silica and similarly washed, gave no detectable amount of polyethylene, thereby indicating that the cocatalyst had been washed from the surface of the silica.

Example 2

The components for This Supported Catalyst Were A2, B1 and C1

3 g Of silica (A2) was slurried in hexane (60 ml) and 5 ml of a 0.1 M solution of the activator (C1) in hexane was added and the mixture agitated for two hours. The slurry was then dried under reduced pressure. 2.8 g Of the resulting solid was reslurried in 40 ml of hexane and 0.7 ml of a 0.2 M solution of metal complex (B1) in hexane was added. The mixture was agitated for two hours and the solvent removed under reduced pressure to yield the product useful in a gas-phase polymerization of ethylene, optionally with 1-butene or 1-hexene comonomer.

Example 3

The components for This Supported Catalyst Were A7, B3 and C2

Under an argon atmosphere, a toluene solution of di($C_{14-18}$ alkyl)methylammonium imidazolate bis[tris (pentafluorophenyl)alumane], 689 µl, 0.0479 M, 33.0 µmol) was diluted to 1500 µl with toluene and added to 1.00 g of triethylaluminum (TEA)-treated silica. The mixture was shaken by hand to break-up clumps and then mechanically agitated for 5 minutes. The volatiles were then removed under reduced pressure. A toluene solution rac-diisopropylamidoborane-bis-($\eta^5$-2-methyl-4-phenylindenyl)zirconium(1,4-diphenyl-1,3-butadene) (1500 µl, 0.020M, 30.0 µmol) was added to the TEA-treated silica. The mixture was shaken by hand to break-up clumps and then mechanically agitated for 5 minutes. The volatiles were then removed under reduced pressure to give a blue solid.

Example 4

The Components for This Supported Catalyst Were A7, B4 and C2

Under an argon atmosphere, a toluene solution of di($C_{14-18}$ alkyl)methylammonium imidazolate bis[tris (pentafluorophenyl)alumane], 689 µl, 0.0479 M, 33.0 µmol) was diluted to 1500 µl with toluene and added to 1.00 g of TEA-treated silica. The mixture was shaken by hand to break-up clumps and then mechanically agitated for 5 minutes. The volatiles were then removed under reduced pressure. A toluene solution rac-dimethylamidoborane-bis-($\eta^5$-2-methyl-4-phenylindenyl)zirconium(1,4-diphenyl-1,3-butadene) (1500 µl, 0.020M, 30.0 µmol) was added to the TEA-treated silica. The mixture was shaken by hand to break-up clumps and then mechanically agitated for 5 minutes. The volatiles were then removed under reduced pressure to give a light blue solid.

Example 5

The Components for This Supported Catalyst Were A7, B2 and C2

Under an argon atmosphere, a toluene solution of di($C_{14-18}$ alkyl)methylammonium imidazolate bis[tris (pentafluorophenyl)alumane], 689 µl, 0.0479 M, 33.0 µmol) was diluted to 1500 µl with toluene and added to 1.00 g of TEA-treated silica. The mixture was shaken by hand to break-up clumps and then mechanically agitated for 5 minutes. The volatiles were then removed under reduced pressure. A toluene solution rac-dimethylsilane-bis-($\eta^5$-2-methyl-4-phenylindenyl)zirconium(1,4-diphenyl-1,3-butadene) (3000 gl, 0.010M, 30.0 µmol) was added to the TEA-treated silica to give a slurry. The mixture then mechanically agitated for 5 minutes. The volatiles were then removed under reduced pressure to give a light blue solid.

Gas Phase Polymerizations

A 2.5-L stirred, fixed bed autoclave was charged with 200 g dry NaCl containing 0.1 g of KH as a scavenger. Stirring was begun at 300 rpm. The reactor was pressurized to 0.8 MPa ethylene and heated to 70° C. 1-hexene (5000 ppm) was introduced to the reactor followed by the addition of hydrogen. In a separate vessel, 0.05 g of catalyst was mixed with an additional 0.1 g KH scavenger. The combined catalyst and scavenger were subsequently injected into the reactor. Ethylene pressure was maintained on demand while hexene and hydrogen were fed to the reactor to maintain their respective concentrations. The temperature of the reactor was maintained at 70° C. by a circulating water bath. After 90 minutes the reactor was depressurized, and the salt and polymer were removed. The polymer was washed with copious quantities of distilled water to remove the salt, dried at 60° C., and then stabilized by addition of a hindered phenol antioxidant (Irganox™ 1010 from Ciba Geigy Corporation) and 133 mg of a phosphorus stabilizer. Activity values were calculated based on ethylene uptake. Results are shown in Table 1.

TABLE 1

| Run | Catalyst | H$_2$ (ppm) | Activity (g/ghb)[1] | Density | I10 | Mw | Mw/Mn |
|---|---|---|---|---|---|---|---|
| 1 | Ex. 3 | 6000 | 140.7 | 0.899 | 0.89 | 180,000 | 3.16 |
| 2 | Ex. 4 | " | 54.0 | 0.898 | 0.57 | 194,000 | 2.56 |
| 3 | Ex. 3 | 8000 | 195.4 | 0.895 | 0.33 | 205,000 | 2.57 |
| 4 | Ex. 4 | 6000 | 66.7 | 0.890 | — | 226,000 | 2.40 |
| 5 | Ex. 3 | 10000 | 236.0 | 0.897 | 0.62 | 180,000 | 2.46 |
| 6 | Ex. 5 | " | 115.6 | 0.893 | 0.25 | 207,000 | 3.73 |
| 7 | Ex. 4 | " | 67.9 | 0.889 | 0.44 | 204,000 | 2.48 |

[1]grams polymer per gram (solid catalyst) · hour · (MPa × 0.1)

Example 6

The Components for This Supported Catalyst Were A3, B2 and C3

Under an argon atmosphere, a toluene solution of di($C_{14-18}$ alkyl)methylammonium 4,5-diphenylimidazolate bis[tris(pentafluorophenyl)borane], 36.0 µmol) was diluted to 2400 µl with toluene and added to 2.00 g of TEA-treated silica. The mixture was shaken by hand to break-up clumps and then mechanically agitated for 15 minutes. Addition of 45 ml of dry hexanes followed by the addition of rac-dimethylsilane-bis-($\eta^5$-2-methyl-4-phenylindenyl) zirconium (1,4-diphenyl-1,3-butadene) (0.0113 gm, 12.0 µmol) to the TEA-treated silica. The mixture was mechanically agitated for 3 hours. The silica was isolated on a medium frit, washed 2× with 25 ml of hexanes and volatiles were then removed under reduced pressure to give a blue solid.

Example 7
The Components for This Supported Catalyst Were A3, B2 and C4

Under an argon atmosphere, a toluene solution of di($C_{14-18}$ alkyl)methylammonium 4,5-dichloroimidazolate bis[tris(pentafluorophenyl)borane], 18.0 μmol) was diluted to 2400 μl with toluene and added to 2.00 g of TEA-treated silica. The mixture was shaken by hand to break-up clumps and then mechanically agitated for 15 minutes. Addition of 45 ml of dry hexanes followed by the addition of rac-dimethylsilane-bis-($\eta^5$-2-methyl-4-phenylindenyl)zirconium (1,4-diphenyl-1,3-butadene) (0.0113 gm, 12.0 μmol) to the TEA-treated silica. The mixture was mechanically agitated for 3 hours. The silica was isolated on a medium frit, washed 2× with 25 ml of hexanes and volatiles were then removed under reduced pressure to give a blue solid.

Example 8
The Components for This Supported Catalyst Were A3, B2 and C5

Under an argon atmosphere, a toluene solution of di($C_{14-18}$ alkyl)methylammonium 4,5-benzimidazolate bis[tris(pentafluorophenyl)borane], 18.0 μmol) was diluted to 2400 μl with toluene and added to 2.00 g of TEA-treated silica. The mixture was shaken by hand to break-up clumps and then mechanically agitated for 15 minutes. Addition of 45 ml of dry hexanes followed by the addition of rac-dimethylsilane-bis-($\eta^5$-2-methyl-4-phenylindenyl)zirconium (1,4-diphenyl-1,3-butadene) (0.0113 gm, 12.0 μmol) to the TEA-treated silica. The mixture was mechanically agitated for 3 hours. The silica was isolated on a medium frit, washed 2× with 25 ml of hexanes and volatiles were then removed under reduced pressure to give a blue-green solid.

Example 9
The Components for This Supported Catalyst Were A5, B2 and C2

Under an argon atmosphere, a toluene solution of di($C_{14-18}$ alkyl)methylammonium imidazolate bis[tris(pentafluorophenyl)alumane], 36.0 μmol) was diluted to 2400 μl with toluene and added to 2.00 g of TEA-treated silica. The mixture was shaken by hand to break-up clumps and then mechanically agitated for 15 minutes. Addition of 45 ml of dry hexanes followed by the addition of rac-dimethylsilane-bis-($\eta^5$-2-methyl-4-phenylindenyl)zirconium (1,4-diphenyl-1,3-butadene) (0.0113 gm, 12.0 μmol) to the TEA-treated silica. The mixture was mechanically agitated for 3 hours. The silica was isolated on a medium frit, washed 2× with 25 ml of hexanes and volatiles were then removed under reduced pressure to give a blue solid.

Example 10
The Components for This Supported Catalyst Were A3, B2 and C6

Under an argon atmosphere, a toluene solution of di($C_{14-18}$ alkyl)methylammonium 1,2,4-triazolate bis[tris(pentafluorophenyl)alumane], 36.0 μmol) was diluted to 2200 μl with toluene and added to 2.00 g of TEA-treated silica. The mixture was shaken by hand to break-up clumps and then mechanically agitated for 15 minutes. Addition of 45 ml of dry hexanes followed by the addition of rac-dimethylsilane-bis-($\eta^5$-2-methyl-4-phenylindenyl)zirconium (1,4-diphenyl-1,3-butadene) (0.0226 gm, 20 24.0 μmol) to the TEA-treated silica. The mixture was mechanically agitated for 3 hours. The silica was isolated on a medium frit, washed 2× with 25 ml of hexanes and volatiles were then removed under reduced pressure to give a light blue solid.

Example 11
The Components for This Supported Catalyst Were A5, B2 and C6

Under an argon atmosphere, a toluene solution of di($C_{14-18}$ alkyl)methylammonium 1,2,4-triazolate bis[tris(pentafluorophenyl)alumane], 36.0 μmol) was diluted to 2200 μl with toluene and added to 2.00 g of TEA-treated silica. The mixture was shaken by hand to break-up clumps and then mechanically agitated for 15 minutes. Addition of 45 ml of dry hexanes followed by the addition of rac-dimethylsilane-bis-($\eta^5$-2-methyl-4-phenylindenyl)zirconium(1,4-diphenyl-1,3-butadene) (0.0226 gm, 24.0 μmol) to the TEA-treated silica. The mixture was mechanically agitated for 3 hours. The silica was isolated on a medium frit, washed 2× with 25 ml of hexanes and volatiles were then removed under reduced pressure to give a light blue solid.

Example 12
The Components for This Supported Catalyst Were A4, B2 and C6

Under an argon atmosphere, a toluene solution of di($C_{14-18}$ alkyl)methylammonium 1,2,4-triazolate bis(tris(pentafluorophenyl)alumane], 72.0 μmol) was diluted to 2300 μl with toluene and added to 2.00 g of TEA-treated silica. The mixture was shaken by hand to break-up clumps and then mechanically agitated for 15 minutes. Addition of 45 ml of dry hexanes followed by the addition of rac-dimethylsilane-bis-($\eta^5$-2-methyl-4-phenylindenyl)zirconium(1,4-diphenyl-1,3-butadene) (0.0226 gm, 24.0 μmol) to the TEA-treated silica. The mixture was mechanically agitated for 3 hours. The silica was isolated on a medium frit, washed 2× with 25 ml of hexanes and volatiles were then removed under reduced pressure to give a light blue solid.

Example 13
The Components for This Supported Catalyst Were A6, B2 and C6

Under an argon atmosphere, a toluene solution of di($C_{14-18}$ alkyl)methyl-ammonium 1,2,4-triazolate bis(tris(pentafluorophenyl)alumane], 72.0 μmol) was diluted to 2300 μl with toluene and added to 2.00 g of TEA-treated silica. The mixture was shaken by hand to break-up clumps and then mechanically agitated for 15 minutes. Addition of 45 ml of dry hexanes followed by the addition of rac-dimethylsilane-bis-($\eta^5$-2-methyl-4-phenylindenyl)zirconium(1,4-diphenyl-1,3-butadene) (0.0226 gm, 24.0 μmol) to the TEA-treated silica. The mixture was mechanically agitated for 3 hours. The silica was isolated on a medium frit, washed 2× with 25 ml of hexanes and volatiles were then removed under reduced pressure to give a light blue solid.

Example 14
The Components for This Supported Catalyst Were A5, B2 and C2

Under an argon atmosphere, a toluene solution of di($C_{14-18}$ alkyl)methylammonium imidazolate bis[tris(pentafluorophenyl)alumane], 36.0 μmol) was diluted to 760 μl with toluene and added to a solution of rac-dimethylsilane-bis-($\eta^5$-2-methyl-4-phenylindenyl)zirconium(1,4-diphenyl-1,3-butadene) (0.0113 gm in 1.5 ml toluene, 12.0 lmol) which was stirred for 15 minutes. The 2.36 ml of premix solution was added to 2.00 g of TEA-treated silica. The mixture was shaken by hand to break-up clumps and then mechanically agitated for 15 minutes, color of solid blue-green. Addition of 45 ml of dry hexanes and mechanically agitated for 1.5 hours. The silica was isolated on a medium frit, washed 2× with 25 ml of hexanes and volatiles were then removed under reduced pressure to give a blue-green solid.

Example 15
The Components for This Supported Catalyst Were A5, B2 and C2

Under an argon atmosphere, a toluene solution of rac-dimethylsilane-bis-($\eta^5$-2-methyl-4-phenylindenyl)zirconium(1,4-diphenyl-1,3-butadene) (0.0113 gm in 2.3 ml toluene, 12.0 μmol) was added to 2.00 g of TEA-treated silica. The mixture was shaken by hand to break-up clumps and then mechanically agitated for 15 minutes. The volatiles were then removed under reduced pressure. To this was added a 2.3 ml toluene solution of di($C_{14-18}$ alkyl)methylammonium imidazolate bis[tris(pentafluorophenyl)alumane], 36.0 μmol). The mixture was shaken by hand to break-up clumps and then mechanically agitated for 15 minutes. Addition of 45 ml of dry hexanes to the mixture followed by mechanically agitating for 1 hour. The silica was isolated on a medium frit, washed 2× with 25 ml of hexanes and volatiles were then removed under reduced pressure to give a blue-greensolid.

Example 16
The Components for This Supported Catalyst Were A8, B2 and C6

Under an argon atmosphere, a toluene solution of rac-dimethylsilane-bis-($\eta^5$-2-methyl-4-phenylindenyl)zirconium(1,4-diphenyl-1,3-butadene) (0.0113 gm in 2.3 ml toluene, 12.0 μmol) was added to 2.00 g of TEA-treated silica. The mixture was shaken by hand to break-up clumps and then mechanically agitated for 15 minutes. The volatiles were then removed under reduced pressure. To this was added a 2.3 ml toluene solution of di($C_{14-18}$ alkyl)methylammonium triazolate bis[tris(pentafluorophenyl)alumane], 36.0 μmol). The mixture was shaken by hand to break-up clumps and then mechanically agitated for 15 minutes. Addition of 45 ml of dry hexanes to the mixture followed by mechanically agitating for 1 hour. The silica was isolated on a medium frit, washed 2× with 25 ml of hexanes and volatiles were then removed under reduced pressure to give a blue-green solid.

Example 17
The Components for This Supported Catalyst Were A8, B2 and C6

Under an argon atmosphere, a toluene solution of di($C_{14-18}$ alkyl)methylammonium triazolate bis[tris(pentafluorophenyl)alumane], 36.0 μmol) was diluted to 760 μl with toluene and added to a solution of rac-dimethylsilane-bis-($\eta^5$-2-methyl-4-phenylindenyl)zirconium(1,4-diphenyl-1,3-butadene) (0.0113 gm in 1.5 ml toluene, 12.0 μmol) which was stirred for 15 minutes. The 2.36 ml of premix solution was added to 2.00 g of TEA-treated silica. The mixture was shaken by hand to break-up clumps and then mechanically agitated for 15 minutes, color of solid blue-green. Addition of 45 ml of dry hexanes and mechanically agitated for 1.5 hours. The silica was isolated on a medium frit, washed 2× with 25 ml of hexanes and volatiles were then removed under reduced pressure to give a blue-green solid.

Polypropylene Polymerizations

Propylene polymerizations were performed in a 1.8-liter, jacketed, reactor that was charged with 625 g of mixed alkanes solvent and about 500 g propylene. Hydrogen, (Δ200 kPa) was added by differential pressure expansion from a 75 mL addition tank. The reactor was heated to 25° C. and allowed to equilibrate. The desired amount of supported catalyst (about 0.05 g) was mixed with hexane and charged to the polymerization reactor through a stainless steel transfer line using nitrogen. The polymerization conditions were maintained for 10 minutes and then the temperature was increased to 60° C. for about 20 minutes. Heat was continuously removed from the reaction through a cooling coil in the jacket. The resulting reaction mixture was removed from the reactor, quenched with isopropyl alcohol, and stabilized by addition of a hindered phenol antioxidant (Irganox™ 1010 from Ciba Geigy Corporation). The solvent was removed in a vacuum oven set at 140° C. by heating the polymer solution for about 16 hours. Results are shown in Table 2.

TABLE 2

| Run | Catalyst | Activity (g/gh)[1] | Tc (° C.) | Mw |
|---|---|---|---|---|
| 8 | Ex. 6 | 610 | 153 | — |
| 9 | Ex. 7 | 730 | 150 | — |
| 10 | Ex. 8 | 292 | 141 | — |
| 11 | Ex. 9 | 102 | 153 | — |
| 12 | Ex. 10 | 1187 | 152 | 220,000 |
| 13 | Ex. 11 | 52 | 150 | 156,000 |
| 14 | Ex. 12 | 92 | 152 | — |
| 15 | Ex. 13 | 565 | 149 | — |
| 16 | Ex. 14 | 141 | 153 | — |
| 17 | Ex. 15 | 112 | 151 | — |
| 18 | Ex. 16 | 1353 | 151 | — |
| 19 | Ex. 17 | 2642 | 152 | — |

[1]grams polymer/gram (solid catalyst) · hour

What is claimed is:

1. A supported catalyst composition for use in an addition polymerization comprising:

A) an inert support;

B) a Group 3–10 or Lanthanide metal complex; and

C) an activator compound capable of causing the metal complex B) to form an active polymerization catalyst, said compound corresponding to the formula:

$$(A^{*+a})_b(Z^*J^*_j)^{-c}_d \qquad (I)$$

wherein:

A* is a cation of charge +a,

Z* is an anion group of from 1 to 50 atoms, not counting hydrogen atoms, further containing two or more Lewis base sites;

J* independently each occurrence is a Lewis acid coordinated to at least one Lewis base site of Z*, and optionally two or more such J* groups may be joined together in a moiety having multiple Lewis acidic functional groups, j is a number from 2 to 12 and a, b, c, and d are integers from 1 to 3, with the proviso that a×b is equal to c×d.

2. A composition according to claim 1 wherein $A^{*+a}$ is an ammonium, sulfonium, phosphonium, oxonium, carbonium, silylium, ferrocenium, $Ag^+$, or $Pb^{+2}$ cation.

3. A composition according to claim 1 wherein Z* is a cyanide, azide, amide and substituted amide, amidinide and substituted amidinide, dicyanamide, imidazolide, substituted imidazolide, imidazolinide, substituted imidazolinide, benzimidazolide, substituted benzimidazolide, tricyanomethide, tetracyanoborate, puride, squarate, 1,2,3-triazolide, substituted 1,2,3-triazolide, 1,2,4-triazolide, substituted 1,2,4-triazolide, 4,5-benzi-1,2,3-triazolide, substituted 4,5-benzi-1,2,3-triazolide, pyrimidinide, substituted pyrimidinide, tetraimidazoylborate and substituted tetraimidazoylborate anions, wherein each substituent, if present, is a halo, hydrocarbyl, halohydrocarbyl, silyl, (including mono-, di- and tri(hydrocarbyl)silyl), silylhydrocarbyl, or halocarbyl group of up to 20 atoms not counting hydrogen, or two such substituents together form a saturated or unsaturated ring system.

4. A composition according to claim 1 wherein J* corresponds to the formula:

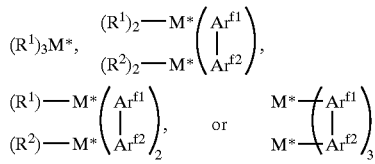

wherein:

M* is aluminum, gallium or boron;

$R^1$ and $R^2$ independently each occurrence are hydride, halide, or a hydrocarbyl, halocarbyl, halohydrocarbyl, dialkylamido, alkoxide, or aryloxide group of up to 20 carbons, with the proviso that in not more than one occurrence is $R^1$ or $R^2$ halide, and $Ar^{f1}$—$Ar^{f2}$ in combination, independently each occurrence, is a divalent fluoro-substituted aromatic group of from 6 to 20 carbons.

5. A composition according to claim 4 wherein J* corresponds to the formula: $BR^1_3$ or $AlR^1_3$ wherein:

$R^1$ independently each occurrence is a $C_{1-20}$ hydrocarbyl, halocarbyl, or halohydrocarbyl radical.

6. A composition according to claim 5 wherein $R^1$ is a fluorinated $C_{1-20}$ hydrocarbyl group.

7. A composition according to claim 6 wherein $R^1$ each occurrence is pentafluorophenyl.

8. A composition according to claim 1 wherein component C) is the ammonium, phosphonium, sulfonium, oxonium, carbonium, silylium, lead (II), silver or ferrocenium salt of: bis(tris(pentafluorophenyl)alumane)cyanide, bis(tris(pentafluorophenyl)alumane)azide, bis(tris(pentafluorophenyl)-alumane)dicyanamide, bis(tris(pentafluorophenyl)alumane)imidazolide, bis(tris(pentafluorophenyl)alumane)-2-undecylimidazolide, bis(tris(pentafluorophenyl)alumane)-4,5-dichloroimidazolide, bis(tris(penta-fluorophenyl)alumane)-2-undecyl-4,5-dichloroimidazolide, bis(tris(pentafluorophenyl)alumane)4,5-diphenylimidazolide, bis(tris(penta-fluorophenyl)alumane)-2-undecyl-4,5-diphenylimidazolide, bis(tris(pentafluorophenyl)alumane)imidazolinide, bis(tris(pentafluorophenyl)alumane)-2-undecylimidazolinide, bis(tris-(pentafluorophenyl)alumane)-5,6-dimethylbenzimidazolide, bis(tris(pentafluorophenyl)alumane)-4,5-bis(heptadecyl)imidazolide, tris(tris(pentafluorophenyl)alumanetricyanomethide, tris(tris(pentafluorophenyl)alumane)puride, tetrakis(tris(pentafluoro-phenyl)alumane)tetraimidazoylborate, bis(tris(heptafluoro-2-naphthyl)alumane)cyanide, bis(tris(heptafluoro-2-naphthyl)alumane)azide, bis(tris(heptafluoro-2-naphthyl)alumane)dicyanamide, bis(tris(heptafluoro-2-naphthyl)alumane)imidazolide, bis(tris(heptafluoro-2-naphthyl)alumane)-2-undecylimidazolide, bis(tris(pentafluorophenyl)alumane)benzimidazolide, bis(tris(penta-fluorophenyl)alumane)-2-undecylbenzimidazolide, bis(tris-(heptafluoro-2-naphthyl)alumane)-5,6-dimethylbenzimidazolide, bis(tris(heptafluoro-2-naphthyl)alumane)-4,5-bis(heptadecyl)imidazolide, tris(trisheptafluoro-2-naphthyl)-alumanetricyanomethide, tris(tris(heptafluoro-2-naphthyl)alumane)puride, tetrakis(tris(heptafluoro-2-naphthyl)alumane)tetraimidazoylborate, bis(tris(pentafluorophenyl)alumane)-1,2,3-triazolide, bis(tris(pentafluorophenyl)alumane)-1,2,4-triazolide, bis(tris(pentafluorophenyl)alumane)-4,5-diphenyl-1,2,3-triazolide, bis(tris(pentafluorophenyl)alumane)-1,2,3-benzatriazolide, bis(tris(pentafluorophenyl)alumane)-5-methyl-1,2,4-triazolide, bis(tris(pentafluorophenyl)alumane)-5-undecyl-1,2,4-triazolide, bis(tris(pentafluorophenyl)borane)cyanide, bis(tris(pentafluorophenyl)borane)azide, bis(tris(pentafluorophenyl)borane)dicyanamide, bis(tris(pentafluorophenyl)borane)imidazolide, bis(tris(pentafluorophenyl)borane)-2-undecylimidazolide, bis(tris(pentafluorophenyl)borane)-4,5-dichloroimidazolide, bis(tris(penta-fluorophenyl)borane)-2-undecyl-4,5-dichloroimidazolide, bis(tris(pentafluorophenyl)borane)-4,5-diphenylimidazolide, bis(tris(penta-fluorophenyl)borane)-2-undecyl-4,5-diphenylimidazolide, bis(tris(pentafluorophenyl)borane)imidazolinide, bis(tris(pentafluorophenyl)borane)-2-undecylimidazolinide, bis(tris(pentafluorophenyl)borane)-5,6-dimethylbenzimidazolide, bis(tris(pentafluorophenyl)borane)-4,5-bis(heptadecyl)imidazolide, tris(tris(pentafluorophenyl)borane tricyanomethide, tris(tris(pentafluorophenyl)borane)puride, tetrakis(tris(pentafluorophenyl)borane)tetraimidazoylborate, bis(tris(heptafluoro-2-naphthyl)borane)cyanide, bis(tris(heptafluoro-2-naphthyl)borane)azide, bis(tris(hepta-fluoro-2-naphthyl)borane)dicyanamide, bis(tris(heptafluoro-2-naphthyl)borane)imidazolide, bis(tris(heptafluoro-2-naphthyl)borane)-2-undecylimidazolide, bis(tris(pentafluorophenyl)borane)benzimidazolide, bis(tris(penta-fluorophenyl)borane)-2-undecylbenzimidazolide, bis(tris-(heptafluoro-2-naphthyl)borane)-5,6-dimethylbenzimidazolide, bis(tris(heptafluoro-2-naphthyl)borane)-4,5-bis(heptadecyl)imidazolide, tris(trisheptafluoro-2-naphthyl)borane tricyanomethide, tris(tris(heptafluoro-2-naphthyl)borane)puride, tetrakis(tris(heptafluoro-2-naphthyl)borane)tetraimidazoylborate, bis(tris(pentafluorophenyl)borane)-1,2,3-benzatriazolide, bis(tris(pentafluorophenyl)borane)-1,2,4-triazolide, bis(tris(pentafluorophenyl)borane)4,5-diphenyl-1,2,3-triazolide, bis(tris(pentafluorophenyl)borane)-5-methyl-1,2,4-triazolide, and bis(tris(pentafluorophenyl)borane)-5-undecyl-1,2,4-triazolide.

9. A composition according to claim 1 wherein component C) is the tri($C_{1-20}$ hydrocarbyl)ammonium-salt of:

bis(tris(pentafluorophenyl)borane)imidazolide, bis(tris(pentafluorophenyl)borane)-2-undecylimidazolide, bis(tris(pentafluorophenyl)borane)benzimidazolide, bis(tris(pentafluorophenyl)borane)-2-undecylbenzimidazolide, bis(tris(pentafluorophenyl)borane)imidazolinide, bis(tris(pentafluorophenyl)borane)2-undecylimidazolinide, bis(tris(pentafluorophenyl)borane)-1,2,3-triazolide, bis(tris(pentafluorophenyl)borane)-1,2,4-triazolide, bis(tris(pentafluorophenyl)borane)-3-(undecyl)-1,2,4-triazolide, bis(tris(pentafluorophenyl)alumane)imidazolide, bis(tris(pentafluorophenyl)alumane)-2-undecylimidazolide,
bis(tris(pentafluorophenyl)alumane)benzimidazolide,
bis(tris(pentafluorophenyl)alumane)-2-undecylbenzimidazolide,
bis(tris(pentafluorophenyl)alumane)imidazolinide,
bis(tris(pentafluorophenyl)alumane)2-undecylimidazolinide,
bis(tris(pentafluorophenyl)alumane)-1,2,3-triazolide,
bis(tris(pentafluorophenyl)alumane)-1,2,4-triazolide, and
bis(tris(pentafluorophenyl)alumane)-3-(undecyl)-1,2,4-triazolide.

10. A slurry phase polymerization of α-olefins comprising contacting at least one alpha olefin under polymerization conditions with the supported catalyst composition according to any one of claims 1–9.

11. A gas phase polymerization of α-olefins comprising contacting at least one alpha olefin under polymerization conditions with the supported catalyst composition according to any one of claims 1–9.

12. The process of claim 11 wherein the polymer product formed has a bulk density greater than 0.3 g/ml.

13. The process of claim 12 wherein propylene is polymerized to form polypropylene.

14. The process of claim 13, wherein component B) is rac-dimethylsilane bis($\eta^5$-2-methyl-4-phenylinden-1-yl) zirconium (II) 1,4-diphenyl-1,3-butadiene.

* * * * *